US 6,653,079 B2

(12) United States Patent
Yang et al.

(10) Patent No.: US 6,653,079 B2
(45) Date of Patent: Nov. 25, 2003

(54) METHODS FOR DETECTION OF DIFFERENCES IN NUCLEIC ACIDS

(75) Inventors: Qinghong Yang, Mountain View, CA (US); Wendy Yang, Mountain View, CA (US); Alla Lishanski, San Jose, CA (US)

(73) Assignee: FreshGene, Inc., Concord, CA (US)

( * ) Notice: Subject to any disclaimer, the term of this patent is extended or adjusted under 35 U.S.C. 154(b) by 0 days.

(21) Appl. No.: 09/804,661

(22) Filed: Mar. 12, 2001

(65) Prior Publication Data

US 2002/0042061 A1 Apr. 11, 2002

Related U.S. Application Data

(60) Provisional application No. 60/188,669, filed on Mar. 11, 2000, provisional application No. 60/228,885, filed on Aug. 29, 2000, provisional application No. 60/234,229, filed on Sep. 21, 2000, provisional application No. 60/234,363, filed on Sep. 22, 2000, provisional application No. 60/242,770, filed on Oct. 23, 2000, and provisional application No. 60/242,840, filed on Oct. 23, 2000.

(51) Int. Cl.[7] .................... C12Q 1/68; C12P 19/34; G01N 33/00; C07H 21/02; C07H 21/04
(52) U.S. Cl. ................ 435/6; 435/91.1; 436/94; 536/23.1; 536/24.3
(58) Field of Search ............... 435/6, 91.1, 183; 436/94, 501; 536/23.1, 24.3, 24.33, 25.3, 25.32

(56) References Cited

U.S. PATENT DOCUMENTS

| | | |
|---|---|---|
| 5,698,400 A | 12/1997 | Cotton et al. |
| 5,824,471 A | 10/1998 | Mashal et al. |
| 6,013,439 A * | 1/2000 | Lishanski et al. ............... 435/6 |

FOREIGN PATENT DOCUMENTS

| WO | WO 97/23646 | 12/1996 |
|---|---|---|
| WO | WO 00/20643 | 10/1999 |

OTHER PUBLICATIONS

Zerbib et al., Coordinated actions of RuvABC in holiday Junction processing. J. Mol. Biol., 281, 621–630.*

(List continued on next page.)

Primary Examiner—Ethan C. Whisenant
Assistant Examiner—Frank Lu
(74) Attorney, Agent, or Firm—Gray Cary Ware & Freidenrich LLP

(57) ABSTRACT

The present invention provides methods for detecting the presence or absence of a difference between two related nucleic acid sequences. In the methods, a target nucleic acid and a reference nucleic acid are contacted under conditions in which they are capable of forming a four-way nucleic acid complex with a branch structure that is capable of migration. Under the contact conditions, if the reference nucleic acid and target nucleic acid are identical, branch migration is capable of going to completion resulting in complete strand exchange. If the reference nucleic acid and target nucleic acid are different, branch migration does not go to completion, resulting in a stable four-way complex. Detection of the stable four-way complex identifies the presence of a difference between the nucleic acids. A stable four-way complex can be detected with molecules that specifically bind such complexes, by gel electrophoresis or by specific isolation of the stable four-way complex.

18 Claims, 11 Drawing Sheets

OTHER PUBLICATIONS

Adams et al., Unwinding of closed circular DNA by the *Escherichia coli* RuvA and RuvB recombination/repair proteins. J. Mol. Biol., 247, 404–417.*

Mezard et al., *Escherichia coli* RuvBL268S: a mutant RuvB protein that exhibits wild–type activities in vitro but confers a UV–sensitive ruv phenotype in vivo. Nucleic Acids Res., 27, 1275–1282, Mar. 1999.*

Panyutin et al., The kinetics of spontaneous DNA branch migration. Proc. Natl. Acad. Sci. USA, 91, 2021–2025, 1994.*

Davies et al., "Formation of RuvABC–Holliday Junction Complexes in Vitro," *Current Biology* vol. 8 No. 12, pp 725–727 (1998).

Panyutin et al., "Formation Of A Single Base Mismatch Impedes Spontaneous DNA Branch Migration," *J Mol Biol.* vol. 230 No. 2, pp 413–24 (1993).

Saiki et al., "Enzymatic Amplification of β–Globin Genomic Sequences and Restriction Site Analysis For Diagnosis of Sickle Cell Anemia," *Science*, vol. 230(4732) pp 1350–4, (1985).

Whitby et al., "Interactions between RuvA and RuvC at Holliday junctions: inhibition of junction cleavage and formation of a RuvA–RuvC–DNA complex," *J Mol Biol* vol. 264(5) pp 878–90 (1996).

* cited by examiner

For each SNP position in question, two versions exist (bi-allelic): either A or a.

Two sets of primers:
- 1st set of primers: LF/LR1/LR2
- 2nd set of primers: RF/RR1/RR2

T1=/=T2, T3=/=T4, T1/T2 =T3/T4 or T1/T2 =/=T3/T4

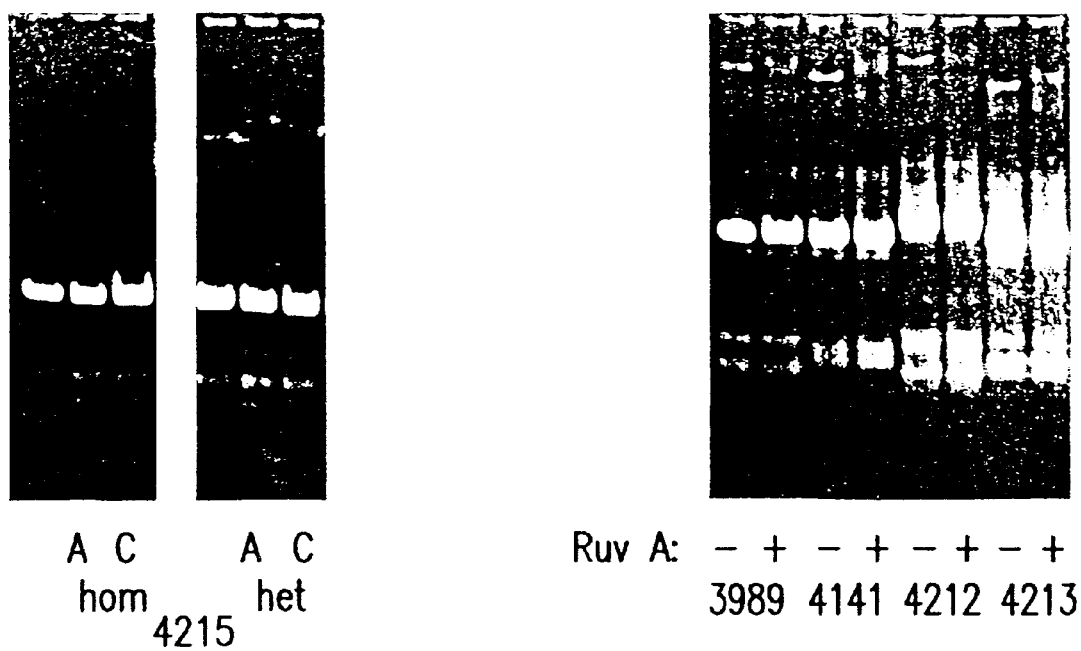
FIG.9A
FIG.9B
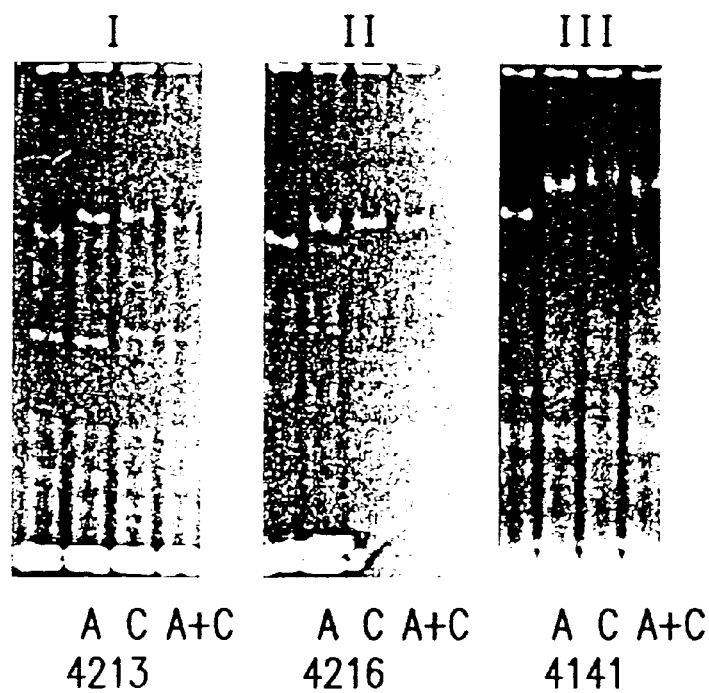
FIG.9C

METHODS FOR DETECTION OF DIFFERENCES IN NUCLEIC ACIDS

1. CROSS REFERENCE TO RELATED APPLICATIONS

This application claims the benefit under 35 U.S.C. § 119 of U.S. Provisional Application No. 60/188,669, filed Mar. 11, 2000, U.S. Provisional Application No. 60/228,885, filed Aug. 29, 2000, U.S. Provisional Application No. 60/234,229, filed Sep. 21, 2000, U.S. Provisional Application No. 60/234,363, filed Sep. 22, 2000, U.S. Provisional Application No. 60/242,770, filed Oct. 23, 2000, and U.S. Provisional Application No. 60/242,840, filed Oct. 23, 2000. The contents of these applications are incorporated herein by reference in their entireties.

2. FIELD OF THE INVENTION

The present invention relates to the field of molecular biology, more particularly nucleic acid hybridization, Holliday junction formation and branch migration. In one aspect, the invention provides methods and reagents for detecting the presence of a difference between two related nucleic acid sequences. In preferred embodiments of the invention, the difference is a mutation, such as a point mutation, deletion or insertion. Practical applications of the invention include, but are not limited to, genotyping, discovery and detection of single nucleotide polymorphisms, characterization and quantitation of polynucleotides, mutation rate detection, gene expression analysis. Furthermore, the invention is capable of distinguishing between homozygous and heterozygous genetic variation.

3. BACKGROUND OF THE INVENTION

The tendency of nucleic acids to bind selectively and specifically to complementary nucleic acids has been exploited in the development of numerous nucleic acid hybridization techniques. Not only are such techniques useful for detecting complementarity and/or identity between nucleic acid sequences (e.g.: quantitating differential gene expression level such as Northern blots, Southern blots and gene expression chip/micro-arrays), but in some cases they are exploited to be used for detecting differences between related nucleic acid sequences.

Current allele-specific-hybridization-based genotyping technology suffers from poor accuracy due to low specificity. In particular, current genotyping technology based on polynucleotide hybridization often displays insufficient specificity to distinguish or identify single nucleotide polymorphisms. For instance, specific DNA strands/oligos containing one version of a specific SNP can hybridize not only to a perfectly matched complementary DNA but also to non-perfectly matched ones such as those contain a second version of the specific SNP. Althought the hybridization is stronger between two perfectly complementary DNA strands than that between two non-perfectly complementary DNA strands (including those that have either a single or multiple base-pair-mismatch between the two complementary strands), a single-base-pair difference is usually too small to render a high enough specificity for SNP scoring. In contrast, gene-expression chips and/or micro-arrays often have much better specificity/accuracy than SNP chips/micro-arrays due to the fact that the hybridization between specific cDNAs and their corresponding oligos/DNA fragments immobilized on the chip/micro-array is very specific. Such hybridization does not necessarily depend on a single-base pair difference between two nucleic acids. The method disclosed herein addresses the problem by combining highly specific allele-specific holiday structure formation with nucleic acid hybridization techniques (e.g.: gene chip/micro-array). As a result, SNP chips/micro-arrays can achieve the same high level of specificity/accuracy as gene-expression chips/micro-arrays.

In Panyutin IG et al's 1993 paper (Panyutin IG, Hsieh P, Formation of a Single Base Mismatch Impedes Spontaneous DNA Branch Migration (1993) J. Mol. Biol., 230:413–24.), a single-stranded oligo that is completely (or partially) complementary to a specific part of single-stranded M13mp18 viral DNA anneals to the viral DNA and form a partial duplex with either 1 (or 2) tail(s) at each end. The partial duplex formed between the oligo and the M13mp18 viral DNA can then form a four-way Holliday-like structure with an invading partial duplex with either 1 (or 2) complementary tails. The four-way Holliday-like structure then undergoes branch migration in the direction away from the tail(s) (It can not branch migrate back towards the tail(s) due to energy barrier: breaking existing H-bonds without forming new ones). For Holliday structures formed between single-tailed partial duplexes, a single (or multiple) base pair difference between the duplex part of oligo/M13mp18 partial duplex and the duplex part of the invading partial duplex poses enough energy barrier (2 H-Bonds→0 H-bond) to impede the branch-migration and prevent the release of the annealed oligo, regardless of the presence or absence of Mg++. For Holliday structure formed between double-tailed partial duplexes, a single base pair difference (substitution, deletion or insertion) between the duplex part of oligo/M13mp18 partial duplex and the duplex part of the invading partial duplex poses enough energy barrier to impede the branch-migration and prevent the release of the annealed oligo ONLY in the presence of Mg++.

One method that has been proposed for detecting differences between related nucleic acid sequences involves forming a complex comprising a Holliday junction between the related sequences. In this method, described in U.S. Pat. No. 6,013,439, each member of at least one pair of non-complementary strands within the complex is labeled. The two labels generate a signal that is dependent upon the labels being in close proximity to one another. If there is a difference in the related nucleic acid sequences, the Holliday junction is stabilized, thus positioning the labels within close proximity to one another and thereby generating a signal. If, on the other hand, no difference exists between the two sequences, the Holliday junction is not stabilized and the complex dissociates into duplexes, eliminating the close proximity between the two labels and attenuating the signal. A determination is made whether a stabilized complex is formed, the presence thereof indicating the existence of a difference between the related sequences.

One problem with the above-identified method of detecting differences between related nucleic acid sequences is that it normally requires the use of labeled PCR primers to generate the labeled nucleic acid strands required for detection of the Holliday junction complex. Particularly when the nucleic acid targeted for analysis is genomic DNA, the use of labeled primers can be problematic owing to the concentration of primer that must be used and the ensuing interference that occurs in the presence of high levels of labeled primers. This is a significant disadvantage, since one of the primary practical applications of the methodology is for the analysis of genomic DNA. Furthermore, the preparation and use of labeled nucleic acids is costly and inconvenient, so that it would be desirable to have available effective methods for determining sequence differences that do not require the use of labeled polynucleotides or primers.

The present invention addresses the problems associated with the use of labeled polynucleotides and primers by providing novel methods and reagents for the rapid and efficient identification of differences between related nucleic acid sequences. As such, the invention constitutes a highly desirable and practical addition to fields of endeavor including molecular biology and medicine.

Based on Panyutin IG and Hsieh P's finding, we designed a genotyping method that allows multiplexing of genotyping assays (tens of thousands of SNPs/mutations can be assayed simultaneously in one assay reaction) and eliminate the requirement of individual PCR reactions. As a result, our method has the potential to dramatically reduce the cost and improve the throughput for genotyping.

4. SUMMARY OF THE INVENTION

In one aspect, the present invention provides methods for detecting the presence or absence of a difference between two related nucleic acid sequences. The methods achieve sensitivities great enough to detect the presence of any difference between the nucleic acids, even single nucleotide polymorphisms. In the methods, a target nucleic acid and a reference nucleic acid are contacted under conditions in which they are capable of forming a four-way nucleic acid complex with a branch structure that is capable of migration. Under the contact conditions, if the reference nucleic acid and target nucleic acid are identical, branch migration is capable of going to completion resulting in complete strand exchange. If the reference nucleic acid and target nucleic acid are different, branch migration does not go to completion, resulting in a stable four-way complex. Detection of the stable four-way complex identifies the presence of a difference between the nucleic acids. A stable four-way complex can be detected with molecules that specifically bind such complexes, by gel electrophoresis or by specific isolation of the stable four-way complex.

In one exemplary embodiment, the present invention provides a method for detecting the presence of a difference between two related nucleic acid sequences. The method involves forming a four-way complex comprising both of the nucleic acid sequences in duplex form, wherein the nucleic acids within the four-way complex are either not labeled or one of the four nucleic acid strands forming the four-way complex has a label, subjecting the four-way complex to conditions allowing branch migration to occur wherein, if a difference between the two related nucleic acid sequences is present, branch migration in said four-way complex ceases and the four-way complex continues to exist as a stable four-way complex; and wherein, if no difference between the two related nucleic acid sequences is present, branch migration in the four-way complex continues until complete strand exchange occurs and the four-way complex resolves into two duplex nucleic acids, subjecting said four-way complex or its resolved duplex products after branch migration to conditions allowing the specific binding of reagent(s) to said four-way complex and the binding of said reagent(s) to said four-way complex produces a detectable signal, and detecting the signal produced upon the specific binding of said reagent(s) to said four-way complex as the presence of said four-way complex, the signal thereof being related to the presence of said difference between said nucleic acid sequences and the failure to detect said signal thereof being related to the lack of difference between said nucleic acid sequences.

In another exemplary embodiment, the present invention provides a method for detecting the presence of a difference between two related nucleic acid sequences. The method involves forming a four-way complex comprising both of the nucleic acid sequences in duplex form, wherein the nucleic acids within the four-way complex are either not labeled or one or more of the four nucleic acid strands forming the four-way complex has a label, subjecting the four-way complex to conditions allowing branch migration to occur wherein, if a difference between the two related nucleic acid sequences is present, branch migration in said four-way complex ceases and the four-way complex continues to exist as a stable four-way complex; and wherein, if no difference between the two related nucleic acid sequences is present, branch migration in the four-way complex continues until complete strand exchange occurs and the four-way complex resolves into two duplex nucleic acids, subjecting said four-way complex or its resolved duplex products after branch migration to conditions allowing the separation of the four-way DNA complex (Holliday structure) from the duplexes DNA and the isolation of the four-way DNA complex. DNA fragments comprising the four-way complex can then be used as probes for SNP scoring through hybridization with oligos/DNA fragments immobilized on chips/microarrays.

5. BRIEF DESCRIPTION OF THE FIGURES

FIG. 1 provides a schematic diagram of an embodiment in accordance with the present invention for detecting any difference between two related nucleic acid sequences using PCR wherein absence of any difference between the two related sequences leads to complete branch migration and the resolution of the Holliday junction complexes;

FIG. 2 provides a schematic diagram of an embodiment in accordance with the present invention for detecting any difference between two related nucleic acid sequences using PCR wherein presence of any difference between the two related sequences blocks branch migration and leads to the formation of stable Holliday junction complexes;

FIG. 3 provides a schematic diagram of showing one way of using Holliday junction specifically binding protein(s) for detecting a difference between two related nucleic acid sequences wherein a mutation is present in one of the two related sequences and branch migration is stopped, leading to the formation of stable Holliday junction complexes that can be detected by using labeled Holliday junction specifically binding protein(s);

FIG. 4 provides a schematic diagram of showing another way of using Holliday junction specifically binding protein(s) for detecting a difference between two related nucleic acid sequences wherein a mutation is present in one of the two related sequences and branch migration is stopped, leading to the formation of stable Holliday junction complexes that can be detected by using labeled Holliday junction specifically binding protein(s);

FIG. 5 provides a schematic diagram of a method of genotyping a target DNA;

FIG. 6A provides a schematic diagram of a method comparing two nucleic acids by resolving four-way complexes immobilized on a solid substrate;

FIG. 6B provides a schematic diagram of a method of detecting a difference between two nucleic acids by detecting stabilized Holliday structures immobilized on a solid substrate;

FIG. 7 is a schematic diagram of an embodiment in accordance with the present invention for determining the genotypes of diploid genomic DNA samples at particular SNP positions by using PCR;

FIG. 8A provides a the results of a typical gel electrophoresis experiment wherein stable Holliday structures are detected;

FIG. 8B provides the results of a typical gel electrophoresis experiment wherein nucleotide differences withinin several pairs are detected;

FIG. 9A illustrates a mobility shift of a stable Holliday structure upon protein binding;

FIG. 9B illustrates specific binding of a stable Holliday structure by RuvA;

FIG. 9C illustrates specific binding of a stable Holliday structure by RuvA, a mutant RuvC, and a mixture of RuvA and mutant RuvC.

6. BRIEF DESCRIPTION OF THE TABLE

Figure 1:
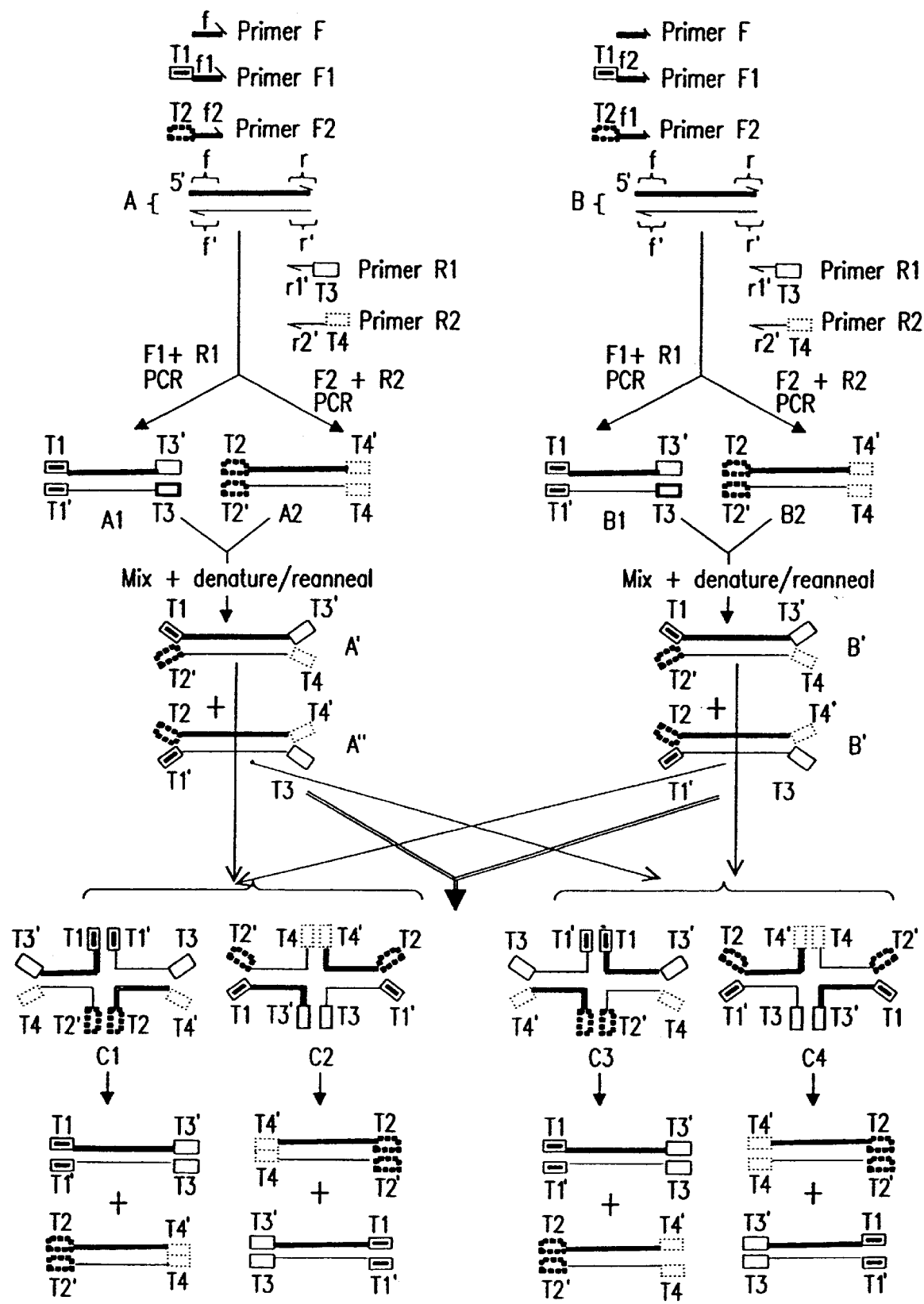

TABLE 1 illustrates an exemplary method for determining the genotypes of diploid genomic DNA samples using PCR.

7. DETAILED DESCRIPTION OF THE PREFERRED EMBODIMENTS

As discussed in the Background section, previous methods for the detection of the presence of a difference between nucleic acids suffer from inaccuracy, low throughput and expense.

As discussed in detail below, the present invention overcomes these and other limitations by providing novel methods for the detection of a difference between nucleic acids. The methods of the present invention display improved accuracy and efficiency when compared to previous methods for detecting a difference between two nucleic acids.

7.1 Abbreviations

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Also, unless specified otherwise, nucleic acid sequences that are represented as a series of one-letter abbreviations are presented in the 5'→3' direction.

7.2 Definitions

As used herein, the terms "nucleic acid" and "polynucleotide" are interchangeable and refer to any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

The terms nucleic acid, polynucleotide, and nucleotide also specifically include nucleic acids composed of bases other than the five biologically occurring bases (adenine, guanine, thymine, cytosine and uracil). For example, a polynucleotide of the invention might contain at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, and 2,6-diaminopurine.

Furthermore, a polynucleotide of the invention may comprise at least one modified sugar moiety selected from the group including but not limited to arabinose, 2-fluoroarabinose, xylulose, and hexose.

It is not intended that the present invention be limited by the source of the polynucleotide. The polynucleotide can be from a human or non-human mammal, or any other organism, or derived from any recombinant source, synthesized in vitro or by chemical synthesis. The nucleotide may be DNA, RNA, cDNA, DNA-RNA, hybrid or any mixture of the same, and may exist in a double-stranded, single-stranded or partially double-stranded form. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, and the like.

The nucleic acid can be only a minor fraction of a complex mixture such as a biological sample. The nucleic acid can be obtained from a biological sample by procedures well known in the art.

A polynucleotide of the present invention can be derivitized or modified, for example, for the purpose of detection, by biotinylation, amine modifictaion, alkylation, or other like modification.

In some circumstances, for example where increased nuclease stability is desired, the invention can employ nucleic acids having modified internucleoside linkages. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide, dimethylene-sulfoxide, dimethylene-sulfone, 2'-O-alkyl, and 2'-deoxy-2'-fluoro phosphorothioate internucleoside linkages are well known in the art (see Uhlman et al., 1990, *Chem. Rev.* 90:543–584; Schneider et al. 1990, *Tetrahedron Lett.* 31:335, and references cited therein).

The term "oligonucleotide" refers to a relatively short, single stranded polynucleotide, usually of synthetic origin. An oligonucleotide typically comprises a sequence that is 8 to 100 nucleotides, preferably, 20 to 80 nucleotides, and more preferably, 30 to 60 nucleotides in length. Various techniques can be employed for preparing an oligonucleotide utilized in the present invention. Such oligonucleotide can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol*, 101, 20–78. Other methods of oligonucleotide synthesis include phosphotriester and phosphodiester methods (Narang, et al. (1979) Meth. Enzymol 68: 90) and synthesis on a support (Beaucage, et al. (1981) Tetrahedron Letters 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

An oligonucleotide "primer" can be employed in a chain extension on a polynucleotide template such as in, for example, an amplification of a nucleic acid. The oligonucleotide primer is usually a synthetic oligonucleotide that is single stranded, containing a hybridizable sequence at its 3'-end that is capable of hybridizing with a defined sequence of the target or reference polynucleotide. Normally, the hybridizable sequence of the oligonucleotide primer has at least 90%, preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random non-specific hybridization. Usually, the number of nucleotides in the hybridizable sequence of the oligonucleotide primer will be at least ten nucleotides, preferably at least 15 nucleotides and, preferably 20 to 50, nucleotides. In addition, the primer may have a sequence at its 5'-end that does not hybridize to the target or reference polynucleotides that can have 1 to 60 nucleotides, 5 to 30 nucleotides or, preferably, 8 to 30 nucleotides.

The term "sample" refers to a material suspected of containing a nucleic acid of interest. Such samples include biological fluids such as blood, serum, plasma, sputum, lymphatic fluid, semen, vaginal mucus, feces, urine, spinal fluid, and the like; biological tissue such as hair and skin; and so forth. Other samples include cell cultures and the like, plants, food, forensic samples such as paper, fabrics and scrapings, water, sewage, medicinals, etc. When necessary, the sample may be pretreated with reagents to liquefy the sample and/or release the nucleic acids -from binding substances. Such pretreatments are well known in the art.

The term "amplification," as applied to nucleic acids refers to any method that results in the formation of one or more copies of a nucleic acid, where preferably the amplification is exponential. One such method for enzymatic amplification of specific sequences of DNA is known as the polymerase chain reaction (PCR), as described by Saiki, et al., (1986) Science, 230: 1350–54. Primers used in PCR can vary in length from about 10 to 50 or more nucleotides, and are typically selected to be at least about 15 nucleotides to ensure sufficient specificity. The double stranded fragment that is produced is called an "amplicon" and may vary in length form as few as about 30 nucleotides to 20,000 or more.

The term "chain extension" refers to the extension of a 3'-end of a polynucleotide by the addition of nucleotides or bases. Chain extension relevant to the present invention is generally template dependent, that is, the appended nucleotides are determined by the sequence of a template nucleic acid to which the extending chain is hybridized. The chain extension product sequence that is produced is complementary to the template sequence. Usually, chain extension is enzyme catalyzed, preferably, in the present invention, by a thermostable DNA polymerase, such as the enzymes derived from *Thermis acquaticus* (the Taq polymerase), *Thermococcus litoralis*, and *Pyrococcus furiosis*.

A "Holliday junction" is the branch point in a four-way junction in a complex of two related (often identical) nucleic acid sequences and their complementary sequences. The junction is capable of undergoing branch migration resulting in dissociation into two double stranded sequences where sequence identity and complementarity extend to the ends of the strands. Holliday junctions, their formation and branch migration are concepts familiar to those of skill in the art, and are described, for example, by Whitby et al., J. Mol. Biol. (1996) 264:878–90, and Davies and West, Current Biology (1998) 8:727–27.

"Branch migration conditions" are conditions under which migration of the Holliday junction branch can proceed along the component polynucleotide strands. Normally in the practice of the invention, conditions are chosen such that migration will proceed only if strand exchange does not result in a mismatch, wherein the formation of a single base mismatch will impede branch migration, resulting in a stabilized Holliday junction or Holliday junction complex. Appropriate conditions can be found, for example, in Panyutin and Hsieh, (1993) J. Mol. Biol., 230:413–24. In certain applications the conditions will have to be modified due to the nature of the particular polynucleotides involved. Such modifications are readily discernible by one of skill in the art without undue experimentation.

A "stabilized" Holliday junction is a junction where a mismatch has stalled branch migration to an extent sufficient that the stabilized Holliday junction is detectable and distinguishable from the duplex DNA that would be released from a Holliday junction involving identical sequences owing to branch migration.

A Holliday junction comprising "complex" refers to a complex of four nucleic acid strands associated through a Holliday junction, which can be inhibited from dissociation into two double stranded sequences by a difference in the sequences and their complements.

Two nucleic acid sequences are "related" when they are either (1) identical to each other, or (2) would be identical were it not for some difference in sequence that distinguishes the two nucleic acid sequences from each other. The difference can be a substitution, deletion or insertion of any single nucleotide or a series of nucleotides within a sequence. Such difference is referred to herein as the "difference between two related nucleic acid sequences." Frequently, related nucleic acid sequences differ from each other by a single nucleotide. Related nucleic acid sequences typically contain at least 15 identical nucleotides at each end but have different lengths or have intervening sequences that differ by at least one nucleotide.

The term "mutation" refers to a change in the sequence of nucleotides of a normally conserved nucleic acid sequence resulting in the formation of a mutant as differentiated from the normal (unaltered) or wild type sequence. Mutations can generally be divided into two general classes, namely, base-pair substitutions and frame-shift mutations. The latter entail the insertion or deletion of one to several nucleotide pairs. A difference of one nucleotide can be significant as to phenotypic normality or abnormality as in the case of, for example, sickle cell anemia.

A "duplex" is a double stranded nucleic acid sequence comprising two complementary sequences annealed to one another. A "partial duplex" is a double stranded nucleic acid sequence wherein a section of one of the strands is complementary to the other strand and can anneal to form a partial duplex, but the full lengths of the strands are not complementary, resulting in a single-stranded polynucleotide tail at at least one end of the partial duplex.

The terms "hybridization," "binding" and "annealing," in the context of polynucleotide sequences, are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is typically achieved by elevating the temperature, increasing the ratio of cosolvents, lowering the salt concentration, and other such methods well known in the field.

Two sequences are "complementary" when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

A "small organic molecule" is a compound of molecular weight less than about 1500, preferably 100 to 1000, more preferably 300 to 600 such as biotin, digoxigenin, fluorescein, rhodamine and other dyes, tetracycline and other protein binding molecules, and haptens, etc. The small organic molecule can provide a means for attachment of a nucleotide sequence to a label or to a support.

7.3 Methods of Detecting A Difference Between Nucleic Acids

The present invention is universal and permits detection of any difference in two related nucleic acid sequences, regardless of whether such difference is known a priori. Such differences include any mutation within a nucleic acid sequence, e.g. a single or multiple base substitution or polymorphism, a deletion or an insertion. Methods of the invention are rapid, convenient, and amenable to automation, and can be conducted in a homogeneous or heterogeneous format. They are ideally suited for rapid mutation pre-screening and genotyping, particularly involving the identification of single nucleotide polymorphisms (SNPs). The disclosed methods are sensitive and quantitative, and are particularly amenable to application with polymerase chain reaction (PCR).

In general, the present invention provides methods and reagents useful for the detection of a difference between two related nucleic acid sequences by determining whether constructs comprising the sequences are capable of forming a stabilized Holliday junction. The present invention provides methods and reagents for generating such constructs for use in the practice of the invention, and methods and reagents useful for stabilizing and detecting Holliday junctions. For instance, in one exemplary embodiment of the invention, the stabilized Holliday junction is detected by means of one or more binding proteins capable of specifically binding a Holliday junction. Specific embodiments of the invention are disclosed herein to illustrate the invention and enable one skilled in the art to practice the invention, and are not intended to limit the scope of the invention.

7.3.1 The Nucleic Acids

The invention provides a novel methodologies for detecting a difference between two polynucleotide sequences by means of the formation of a stabilized Holliday structure involving polynucleotide constructs comprising the sequences, as illustrated in FIG. 1. For purposes of describing the invention, it will be convenient to refer to the two sequences being compared as a target sequence and a reference sequence. The reference sequence is typically a polynucleotide of substantially known sequence, and the target sequence is a related sequence for which it is desired to detect whether there is a difference relative to the reference sequence.

The sequences are related in the sense that the sequences are either identical, or would be identical if not for some difference between the two sequences. In preferred embodiments of the invention, the difference is a substitution, deletion or insertion variation or mutation, such as but not limited to a single nucleotide polymorphism (SNP). Typically, the target sequence and the reference sequence are prepared as a pair of sequences that are capable of forming a partial duplex according to the methods described in detail below.

A typical partial duplex A' is illustrated in FIG. 1. Partial duplex A' comprises a complementary duplex region and one or more tail regions. A complementary duplex region comprises a target sequence or a reference sequence annealed to its complement. Other examples of partial duplexes are illustrated as A", B' and B".

In partial duplex A', one tail region comprises the oligonucleotide tails T1 and T2'. Similarly, a second tail region comprises the oligonucleotide tails T3' and T4. Tail T1, T2', T3' and/or T4 can be linked to the target sequence via any linkage known to those of skill in the art for linking polynucleotides. They can be linked directly via a covalent bond or via a linker. The linker can be a polynucleotide or any other linker known to those of skill in the art. Preferably, tail T1 and/or T3' is linked to the target sequence directly via a phosphodiester linkage. In a similar fashion, tail T1, T2, T3, T4, T1', T2', T3' and/or T4' can be linked to a target sequence or a reference sequence.

In some embodiments of the invention, a partial duplex has one tail region. For instance, partial duplex A' has one tail region when T1 is 0 bp in length and T2' is 0 bp in length while T3'>0 bp and T4 >0 bp (or, alternatively, when T1>0 bp and T2'>0 bp while T3' and T4 are both 0 bp in length). In other embodiments of the invention, a partial duplex has two tail regions. For instance, the partial duplex illustrated in FIG. 1 has two tail regions when T1, T2', T3' and T4 are all greater than 0 bp in length. Tails T1, T2', T3' and T4 are preferably 5 bp–500 bp and more preferably 5 bp–55 bp.

All four tails are comprised of sequences that unrelated to each other and to the template DNA, or alternatively, one of the pair of polynucleotide tails at each terminus of the partial duplexes (T1/T2' or T3'/T4) can be template DNA sequences. Preferably, a tail is capable of hybridizing with another sequence that complements the tail without interference from the target sequence, the reference sequence or from other tails.

In order to form a four-way structure, two or more partial duplexes are prepared with the same target sequence and a corresponding reference sequence. For instance, partial duplexes A' and B", illustrated in FIG. 1, are capable of forming a four-way structure under the appropriate conditions. In FIG. 1, partial duplex A' comprises the tails T1, T2', T3', and T4. Another partial duplex B" comprises the tails T1', T2, T3 and T4'. Each pair of polynucleotide tails at each end of the partial duplexes, e.g., T1/T2', T2/T1', T3'/T4, T3/T4' are not complementary and will not anneal to one another under the applicable conditions. However, tail T3' at the right end of partial duplex A' is complementary to, and hence can hybridize with, tail T3 at the right end of partial duplex B". Tail T4 at the right end of partial duplex A' is complementary to, and hence can hybridize with, tail T4' at the right end of partial duplex B". Tail T1 at the left end of partial duplex A' is complementary to, and hence can hybridize with, tail T1 at the left end of partial duplex B". Tail T2' at the left end of partial duplex A' is complementary to, and hence can hybridize with, tail T2 at the left end of partial duplex B".

7.3.2 Preparation of Nucleic Acids

The partial duplexes described above can be prepared by any method known to those of skill in the art for the preparation of polynucleotides or nucleic acids. For instance, the partial duplexes can be prepared by standard recombinant, synthetic or PCR techniques, or a combination thereof. In addition, the partial duplexes, or portions thereof such as the target or reference sequence, can be isolated from natural sources. Exemplary methods of preparing sequences that are capable of forming partial duplexes are described in U.S. Pat. No. 6,013,439, which is hereby incorporated by reference in its entirety. In a preferred embodiment of the invention, PCR techniques are used to generate partial duplexes. FIG. 1 illustrates the preparation of partial duplexes A', A", B' and B" by PCR. Partial duplexes such as A' and B" can be used to detect a difference between a target sequence and a reference sequence. A can be a target sequence and B a reference sequence, or vice versa.

To determine if there is any difference between the two related DNA sequences, duplex A and B are amplified, either separately or jointly, by standard PCR using a common set of primers made up of one or more forward primers and two reverse primers R1& R2. R1 and R2 can either share the same 3' end (r'=r1'=r2') that hybridizes to the same part of template DNA or the 3' end of R1 and R2 can hybridize to different parts of the template DNA (r1'≠r2'). As illustrated in FIG. 1, forward primer F1 or forward primer F2 can be used in the PCR reaction. If forward primer F1 is used, duplexes with T1/T1'tails will be generated such as A1. If forward primer F2 is used, duplexes with T2/T2' tails will be generated such as A2. Two forward primers can also be used to generate partial duplexes at the end corresponding to the forward primer. For instance, using forward primers F1 and F2 in the same PCR reaction generates sequences that can be used to produce partial duplexes A' and A". In addition, a forward primer with no tails can be used to generate a duplex with no tails at the end corresponding to the forward primer.

Note that in general the primers need not be labeled, but that in certain applications the labeling of one or more primers can be desirable. In a preferred embodiment of the invention, the distance between the binding sites for the forward and reverse primers is at least 1 base pair, preferably in the range of 1–600 base pairs or 5–600 base pairs, more preferably in the range of 5–100 base pairs, depending on the desired purpose of the application and the nature of the polynucleotide of interest.

PCR amplification according to the invention involves temperature cycling to denature duplexes, oligonucleotide primer annealing, and primer extension by thermal-stable template dependent nucleotide polymerase. The temperatures for the present method for the amplification by PCR generally range from about 50° C. to 100° C., more usually from about 60° C. to 95° C. Relatively low temperatures of from about 50° C. to 80° C. are employed for hybridization steps, while denaturation is carried out at a temperature of from about 80° C. to 100° C. and extension is carried out at a temperature of from about 70° C. to 80° C., usually about 72° C. to 74° C. Generally, the time period for conducting the method is from about 10 seconds to 10 minutes per cycle and any number of cycles can be used from one to as high as 60 or more, usually 10 to 50, frequently 20 to 45. Suitable PCR protocols are known in the art and can be found, for example, in Sambrook et al., *Molecular Cloning: A Laboratory Manual*, $2^{nd}$ ed., Cold Spring Harbor Laboratory Press, New York (1989), or arrived at by the skilled artisan without undue experimentation.

The PCR amplification employs convergent oligonucleotide primers designed to be complementary to and anneal to sequences flanking the area of the nucleic acids to be amplified. The primers are designed such that the 3' portion is at least 90%, preferably 95%, and most preferably 100% complementary to a portion of the strand to be amplified. The complementary portion of the primer should be long enough to hybridize selectively to the target or reference sequence under the primer annealing conditions employed for the reaction. Usually, the number of nucleotides in the hybridizable sequence of the primer will be at least 10, preferably at least 15 nucleotides, and more preferably 20 to 50 nucleotides in length. In some cases substantially all of the primer is complementary to the target sequence, such as for example the F primer in FIG. 1. In other cases, the 5' end of the primer is not complementary to the target, in which case this non-complementary sequence will be incorporated at the end of the resulting amplicon. The non-complementary end can have 1 to 60 or more nucleotides, 5 to 30 nucleotides or, preferably, 8 to 30 nucleotides. It is by means of such primers that the oligonucleotide tails at the end of the partial duplexes are generated. Such primers can also be used to generate amplicon intermediates capable of recognition by a universal primer for the production of the partial duplexes of the invention.

The concentration of oligonucleotide primers used in the PCR amplification will be at least as great as the number of copies desired and will usually be in the range of 1 nM to 1 mM, preferably 100 nM to 110 μM. For the amplification of genomic DNA, about 500 nM–1000 nM for the forward primers and ~250 μM–500 μM for each of the two reverse primers is preferred, i.e, similar to the conditions used to amplify an STS (sequence tagged site). When cloned DNA fragments are being amplified, lower primer concentrations are sufficient, for example about 25 nM–250 nM.

The entire sequence of the forward primer F hybridizes with the template DNA, i.e., both A and B. Forward primers F1 and F2 can share their 3' end (f1=f2) and hybridize with the same part of template DNA (reference and target DNA), or alternatively, primer F1 and F2 can have different 3' ends and therefore hybridize with different parts of template DNA (f1≠f2). In addition, F1 has a 5'-end portion (T1) that does or does not hybridize with the template DNA. Likewise, F2 has a 5'-end portion (T2) that does or does not hybridize with the template DNA. The two reverse primers R1 and R2 can share a common 3'-end portion (r'=r1'=r2') that hybridizes with the same part of template DNA, or alternatively, primer R1 and R2 can have different 3' end and therefore hybridize with different part of template DNA. In addition, R1 has a 5'-end portion (T3) that does not hybridize with the template DNA. Likewise, R2 has a 5'-end portion (T4) that is not complementary to and hence does not hybridize with the template DNA. T3 is not related with T4, i.e., the complementary strand of T3 (T3') is not complementary to T4 and the complementary strand of T4 (T4') is not complementary to T3. As a result, T4' will not hybridize with T3 under the conditions employed in the method. Multiple rounds of PCR amplification will result in the formation of a number of DNA products, including the component strands of the four tailed partial duplexes A', A", B', B" (FIG. 1). The tailed duplexes are formed by adjusting the temperature of the solution so that the component strands can hybridize to form the desired partial duplexes. Note that a number of other duplexes will also be formed. These unintended products generally do not pose a problem because a sufficient number of partial duplexes are formed under the conditions described above.

Each tailed partial duplex A' is comprised of a duplex of two complementary nucleic acid strands of duplex A and, at one end of the duplex, two non-complementary oligonucleotide tails T3' and T4. Depending on the choice of forwarding primer, partial duplex A' can have either zero, one or two tails at the other end of the partial duplex (if T1=0 & T2=0, then a partial duplex can be produced with no tails at left end; if T1=0 or T2=0, then a partial duplex can be produce with one tail at the left end; if T1≠T2≠0, then a partial duplex can be produced with two non-complementary tails at the left end). Each tailed partial duplex A" is comprised of a duplex of two complementary nucleic acid strands of duplex A and, at one end of the duplex, two non-complementary oligonucleotide tails T4' and T3. Depending on the choice of forwarding primer, partial duplex A" can have either zero, one or two tails at the other end of the partial duplex (see above). Each tailed partial duplex B' is comprised of a duplex of two complementary nucleic acid strands of duplex B and, at one end of the duplex, two non-complementary oligonucleotide tails T3' and T4. Depending on the choice of forwarding primer, partial duplex B' can have either zero/one/two tails at the other end of the partial duplex (see above). Each tailed partial duplex B" is comprised of a duplex of two complementary nucleic acid strands of duplex B and, at one end of the duplex, two non-complementary oligonucleotides T4' and T3. Depending on the choice of forwarding primer, partial duplex B" can have either zero, one or two tails at the other end of the partial duplex (see above).

When primers F1, F2, R1 and R2 are used to produce the partial duplexes A', B', A", B" while T1≠T2≠T3≠T4, f1≠f2, r1'≠r2' or r1'r2', it is normally convenient to perform the PCR so that partial duplexes A', A", B' and B" are produced simultaneously, by the concomitant inclusion in the reaction of A and B (the target DNA and reference DNA) with primers F1/R1 and F2/R2. It should be noted however, that the various replications and amplifications could also be performed separately if so desired. For example, the amplification of A and B can be achieved in separate reactions using primers F1/R1 or F2/R2, as depicted in FIG. 1. The resulting tailed amplification products could then be combined under the appropriate conditions to form partial duplexes A', A", B' and B" (FIG. 1).

When primers F1, F2, R1 and R2 are used to produce the partial duplexes A', B', A", B" while T1≠T2≠T3≠T4, f1≠f2, r1'≠r2', it is very important that PCR amplification products A1& B1 (by using F1/R1, see FIG. 1) cover more template DNA than A2& B2 (by using F2/R2, see FIG. 1) at both the left and the right end (in other words, f1is more up-stream than f2 and r1'is more down-stream than r2'); alternatively, PCR amplification products A1& B1 (by using F1/R1, see FIG. 1) cover less template DNA than A2& B2 (by using F2/R2, see FIG. 1) at both the left and the right end (in other words, f1 is more down-stream than f2 and r1'is more up-stream than r2'). Please note that it is useless/irrelevant to have tail T1 and T3 (therefore preferably: T1=T3=0 bp) while PCR amplification products A1& B1 (by using F1/R1, see FIG. 1) cover more template DNA than A2& B2 (by using F2/R2, see FIG. 1) at both the left and the right end. By the same token, it is useless/irrelevant to have tail T2 and T4 (therefore preferably: T2=T4=0 bp) while PCR amplification products A1& B1 (by using F1/R1, see FIG. 1) cover less template DNA than A2& B2 (by using F2/R2, see FIG. 1) at both the left and the right end. As discussed above, it is normally convenient to perform the PCR so that partial duplexes A', A", B' and B" are produced simultaneously, by the concomitant inclusion in the reaction of A and B (the target DNA and reference DNA) with primers F1/R1 and F2/R2. It should be noted however, that the various replications and amplifications could also be performed separately if so desired. For example, the amplification of A and B can be achieved in separate reactions using primers F1/R1 or F2/R2, as depicted in FIG. 1. The resulting tailed amplification products could then be combined under the appropriate conditions to form partial duplexes A', A", B' and B" (see FIG. 1).

When primers F, R1 and R2 are used to produce the partial duplexes A', B', A", B"while T1=T2 (preferably T1=T2=0 bp), T3≠T4, f1=f2=f, r1'=r2' or r1'≠r2', it is normally convenient to perform the PCR so that partial duplexes A', A", B' and B" are produced simultaneously, by the concomitant inclusion in the reaction of the A and B (the target and reference) and the primers F, R1 and R2. It should be noted however, that the various replications and amplifications could also be performed separately if so desired. For example, the amplification of A and B can be achieved in separate reactions using primers F, R1 and R2, and the resulting tailed amplification products could then be combined under the appropriate conditions to form partial duplexes A', A", B' and B". Alternatively, A and B could initially be amplified using F and only one of the R primers (either R1 or R2), and then later the other R primer could be added and additional rounds of amplification undertaken, either in the absence or presence of the first used R primer.

All these and other protocol variations, all of which result in the desired tailed partial duplexes A', A", B' and B", will be apparent to the skilled artisan and fall within the scope of the instant invention.

7.3.3 Formation of a Four-way Structure

In order to detect a difference between sequences A and B, partial duplexes (A', A", B', B") comprising sequences A and B are brought into contact under conditions where the complementary tails can anneal to one another, thereby initiating the formation of a four-stranded complex (Holliday junction), as depicted in FIG. 1. The resulting complexes C1, C2, C3, C4 are subjected to conditions where branch migration can occur. Branch migration is restricted from proceeding in the direction of the tails, because the tails on a given partial duplex are not complementary to one another, e.g., T1 is not complementary to T2'. However, branch migration can occur in the other direction to the extent that the reference and target sequences are the same. If the two sequences are identical, branch migration can proceed to the ends of the strands, resulting in the dissociation of the complex into two duplexes, each comprising one strand from each of the original partial duplexes. On the other hand, if the target and reference sequences are different, branch migration past this point of difference will result in a mismatch in the newly formed duplex. Under the conditions used in the practice of the instant invention, the presence of such a difference will actually block branch migration, resulting in a stabilized Holliday junction complex. As a result, the presence of a difference between the two sequences is manifested in the creation of a stabilized Holliday junction that, in the absence of the difference, would resolve into two duplexes.

It will be apparent to the skilled artisan that the right terminus of the tailed partial duplex A' has, as the end part of each strand, sequence T4 and T3', respectively, that are complementary to T4' and T3, respectively, that are tails at the right terminus of B" and are not complementary to each other. When four-tailed partial duplexes A', A", B', B" are present in the same solution under the appropriate conditions, two four-way Holliday junction (complex C1 and C2) comprising partial duplex A' and B" can form. One can form as the result of the hybridization of tail T1 of A' with tail T1'of B" and hybridization of tail T2' of A' with tail T2 of B". Another can form as a result of the hybridization of tail T3' of A' with tail T3 of B" and the hybridization of tail T4 of A' with tail T4' of B". In addition, two more four-way Holliday junction complexes C3 and C4 from partial duplexes A"and B'. One can form when tail T1'of A"hybridizes with tail T1 of B' and when tail T2 of A"hybridizes with tail T2' of B'. The other can form when tail T3 of A"hybridizes with tail T3' of B' and when tail T4' of A"hybridizes with T4 of B'.

In addition, four tailed partial duplexes A', A", B' and B" can form concatemers. For instance, three partial duplexes B", A' and a second partial duplex B" can form a concatamer with two Holliday junctions. However, concatemers do not prevent the detection of differences between sequence A and sequence B. If sequences A and B are identical, then migration of both Holliday structure branches in the B"-A'-B" should go to completion resulting in resolution of the entire concatemer into two duplexes. If there is a difference between sequences A and B, then both Holliday structures will be stabilized. Detection of the stabilized Holliday structures will indicate the difference between sequences A and B.

The skilled artisan using the teaching provided herein and knowledge generally available to the skilled artisan can determine appropriate conditions for hybridization of the tails and the resulting formation of a Holliday junction of any specific duplexes. See, for example, Sambrook et al., supra., Panyutin et al., supra, and U.S. Pat. No. 6,013,439.

Figure 2:
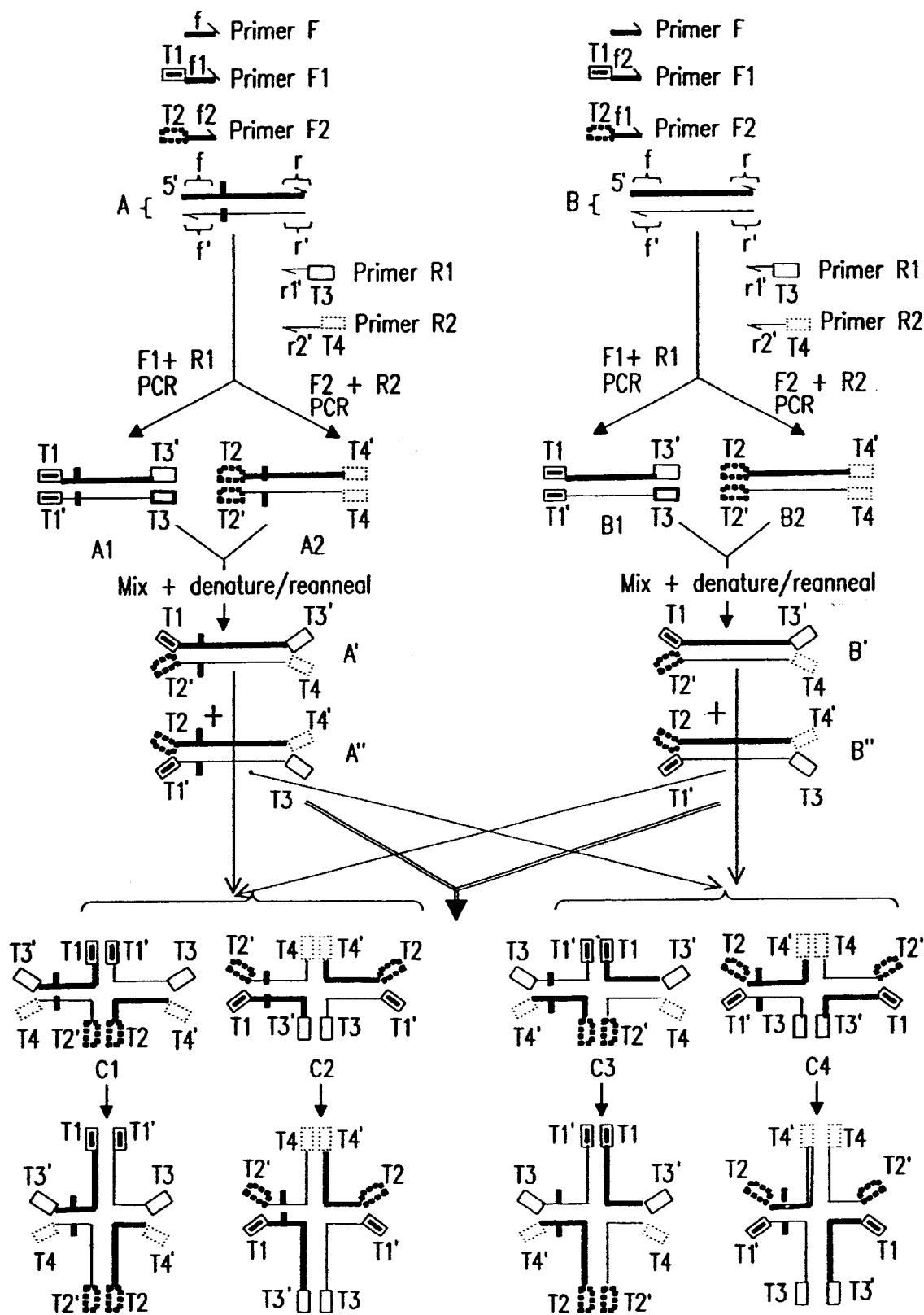

The Holliday junction complexes C1, C2, C3 and C4 are subject to branch migration conditions wherein, because tails T1 and T2 and tails T3 and T4 are different, the branch migration can only proceed away from the tails whose hybridization initiates four-way Holliday complex formation. If there is no mismatch between A and B, the branch migration of complex C1, C2, C3 and C4 can proceed away from the tail all the way to the other end of the partial duplexes. As a result, each of the four Holliday complexes C1, C2, C3 and C4 resolve into duplexes (FIG. 1). Alternatively, if there is a mismatch or mismatches between A and B, the branch migration of complex C1, C2, C3 and C4 proceeding in the direction away from the tail is halted by the mismatch and stabilized Holliday junction complexes C1, C2, C3 and C4 form (FIG. 2). In one embodiment of the invention, branch migration is conducted in the presence of an ion such as $Mg^{++}$, which enhances the tendency of a mismatch to impede spontaneous DNA migration and hence stabilizes Holliday junction complexes involving such a mismatch. A preferred concentration range for $Mg^{++}$ is 1 to 10 mM. It should be noted that stabilization can be achieved by means of other ions, particularly divalent cations such as $Mn^{++}$ or $Ca^{++}$, or by a suitable combination of ions. In a particularly preferred embodiment, branch migration is achieved by incubation at 65° C. for about 20–120 minutes in buffer containing 4 mM $MgCl_2$, n50 mM KCl, 10 mM Tris-HCl, PH 8.3. A description of branch migration conditions suitable for the formation of stabilized Holliday junction as a consequence of a single base mismatch can be found, for example, in Panyutin and Hsieh, (1993) J. Mol. Biol., 230:413–24, which is hereby incorporated by reference in its entirety.

7.3.4 Detection of Holliday Structures

It follows that the detection of the stable four-way Holliday junction complexes (C1, C2, C3 or C4) can be used as to indicate the presence of a difference between DNA sequence A and B. The absence of stabilized four-way Holliday complexes, on the other hand, can be used to indicate the lack of a difference between DNA sequence A and B. According to the present invention, the stabilized Holliday junction indicative of a difference between nucleic acids A and B is detected by any of the means described below. For instance, a stabilized Holliday junction can be detected by a molecule or molecules capable of specifically recognizing and binding a Holliday junction,.

7.3.4.1 Detection with Molecules Specific for Four-Way Nucleic Acid Complexes

In one embodiment, a molecule or molecules with specificity for a Holliday structure is used to detect the presence of a stabilized Holliday structure and thereby the presence of a difference between polynucleotide sequence A and polynucleotide sequence B.

The presence of a Holliday structure can be detected with any molecule or molecules known to those of skill in the art to specifically bind Holliday structures. In a preferred embodiment, a protein or proteins is used to bind and detect the formation of a stabilized Holliday junction. Many proteins from various organisms have been shown specifically bind to Holliday junctions. Those proteins include but are not limited to: RuvA, RuvC, RuvB, RusA, RuvG of *E. coli*; proteins/mutants derived from RuvA, RuvC, RuvB, RusA, RuvG. In addition, such proteins include homologs (including functional homologs) of RuvA, RuvC, RuvB, RusA, RuvG from various other organisms, such as the homologs of RuvA, RuvC, RuvB, RusA, and RuvG derived from mammals, Cce1 and spCce1 from yeast, Hjc from *Pyrococcus furiosusa*, and various other resolvases and recombinases that can specifically bind to Holliday structures.

In particularly convenient embodiments of the invention, thermostable proteins are used to detect the presence of a Holliday structure. Such thermostable proteins include thermostable homologs of RuvA, RuvC, RuvB, RusA, and RuvG that are derived from thermophilic organisms—organisms selected from the group consisting of *Thermus aquaticus, Thermus flavus, Thermus thermophilus* and other thermophilic organisms known to those of skill in the art. Hjc from *Pyrococcus furiosusa* is one good example of an appropriate thermostable protein with specificity for Holliday structures.

The preparation and properties of a number of such proteins useful in the practice of the present invention have been described, for example, in the following list of literature references, all of which are incorporated herein in their entirety: Davies and West, supra; Whitby et al., supra; Iwasaki H,. et al. 1992. *E. coli* RuvA and RuvC proteins specifically interact with Holliday Junctions and promote branch migration. Genes Dev. 6:2214–20; Parsons CA, et al. 1992. Interaction of *E. Coli* RuvA and RuvB proteins with synthetic Holliday junctions. Proc. Natl. Acad. USA 89:5452–56; Traneva IR, et al. 1992. Purification and properties of the RuvA and RuvB proteins of *E. coli*. *Mol. Gen. Genet.* 235:1–10; Rafferty J B, et al. 1996. Crystal structure of the DNA recombination protein RuvA and a model for its binding to the Holliday junction. *Science* 274:415–21; Hargreaves D., et al. 1999. Crystalization of *E. coli* RuvA complexed with a synthetic Holliday junction. Acta Crystallogr D. Biol Crystallogr 55(Pt 1):263–5; Hargreaves D., et al. 1998. Crystal structure of *E. coli* RuvA with bound DNA Holliday junction at 6A resolution. Nature Struct Biol. 5(6):441–6; Dunderdale H J, et al. 1994. Cloning, overexpression, purification, and characterization of the *E. coli* RuvC Holliday junction resolvase. J Biol Chem 267 (7):5187–94; Ariyoshi M, et al. 1994. Atomic structure of the RuvC resolvase: a Holliday junction specific endo nuclease from *E. coli*. Cell 78(6): 1063–72; Sharples G J, et al. 1994. Processing of intermediates in recombination and DNA repair: identification of a new endonuclease that specifically cleaves Holliday junction. EMBO 13(24):6133–42; Rice P, et al. 1995. Structure of the bacteriophage Mu transposase core: a common structural motif for DNA transposition and retroviral integration. Cell 82(2):209–20; Bujacz G., et al. 1995. High-resolution structure of the catalytic domain of avian sarcoma virus integrase. J. Mol Biol 253(2):333–46; Rice P. et al. 1996. Retroviral integrases and their cousins. Curr Opin Struct Biol 6(1):76–83; Suck D. 1997. DNA recognition by structure-selective nucleases. Biopolymer 44(4):405–21; White M F, et al. 1997. The resolving enzyme CCE1 of yeast opens the structure of the four-way junction. J Mol Biol 266(1):122–34; Whitby M C, et al. 1997. A new Holliday junction resolving enzyme from *S. pombe* that is homologous to CCE1 from *S. cerevisiae*. J Mol Biol 271(4):509–22; Bidnenko E, et al. 1998. *Lactococcus lactis* phage operon coding for an endonuclease homologous to RuvC. *Mol Microbiol* 28(4): 823–34; Raaijmakers H, et al. 1999. X-ray structure of T4 endonuclease VII: a DNA junction resolvase with a novel fold and unusual domain-swapped dimer achitecture. *EMBO*. 18(6):1447–58; Komori K, et al. 1999. A Holliday junction resolvase from *Pyrococcus furiosus*: functional similarity to *E. coli* RuvC provides evidence for conserved mechanism of homologous recombination in Bacteria, Eukarya, and Archaea. Proc Natl Acad Sci USA. 96(16):8873–8; Komori K, et al. 2000. Mutational analysis of the *Pyrococcus furiosus* Holliday junction resolvase Hjc revealed functionally important residues for dimer formation, junction DNA binding and cleavage activities. J Biol Chem.(September/2000 issue); Sharples G J, et al. 1999. Holliday junction processing in bacteria: insight from the evolutionary conservation of RuvABC, RecG, and RusA. J bacteriol 181(8);5543–50; Sharples G J, et al. 1993. An *E. coli* RuvC mutant defective in cleavage of synthetic Holliday junctions. Nucleic Acid Research, 21(15): 3359–64.

Proteins specifically bound to a Holliday structure can be detected by methods known to those of skill in the art for detecting and/or visualizing proteins. In fact, one advantage of the instant invention is that is allows for the detection of stable Holliday junctions without the use of labeled nucleic acids. In a preferred embodiment, at least one Holliday junction-specific binding protein, i.e., a protein capable of selectively recognizing and binding a Holliday junction, is labeled with at least one label and subjected to conditions that allow said protein(s) to bind to a stable Holliday junction such as complex C1, C2, C3 and/or C4. The binding of said proteins to the Holliday junction produces some signal(s) that can be detected, preferably in a quantitative way. Said signals can be used as indicators for the presence and quantity of stable Holliday junctions, and in turn, as indicators for the presence and quantity/ratio of mismatched DNA in DNA polymorphism analysis.

In a preferred embodiment, the instant invention employs at least one labeled protein to detect the Holliday junction. The label can be endogenous to the protein, e.g., the natural fluorescence of a protein resulting from the fluorescence of amino acids such as tryptophan, tyrosine, or phenylalanine, or a protein side-chain capable of reacting in a detectable manner. The label can be attached to the protein, either during translation or post-translationally. Suitable labels include, but are not limited to, fluorescent molecules (including, for example, fluorescein, rhodamine, and fluorescent proteins and peptides such as GFP and GFP variants and analogs), radioactive groups, solid surfaces, oligonucleotides, enzymes, dyes, chemiluminiscent groups, coenzymes, enzyme substrates, ligands, receptors and small organic molecules.

Figure 3:
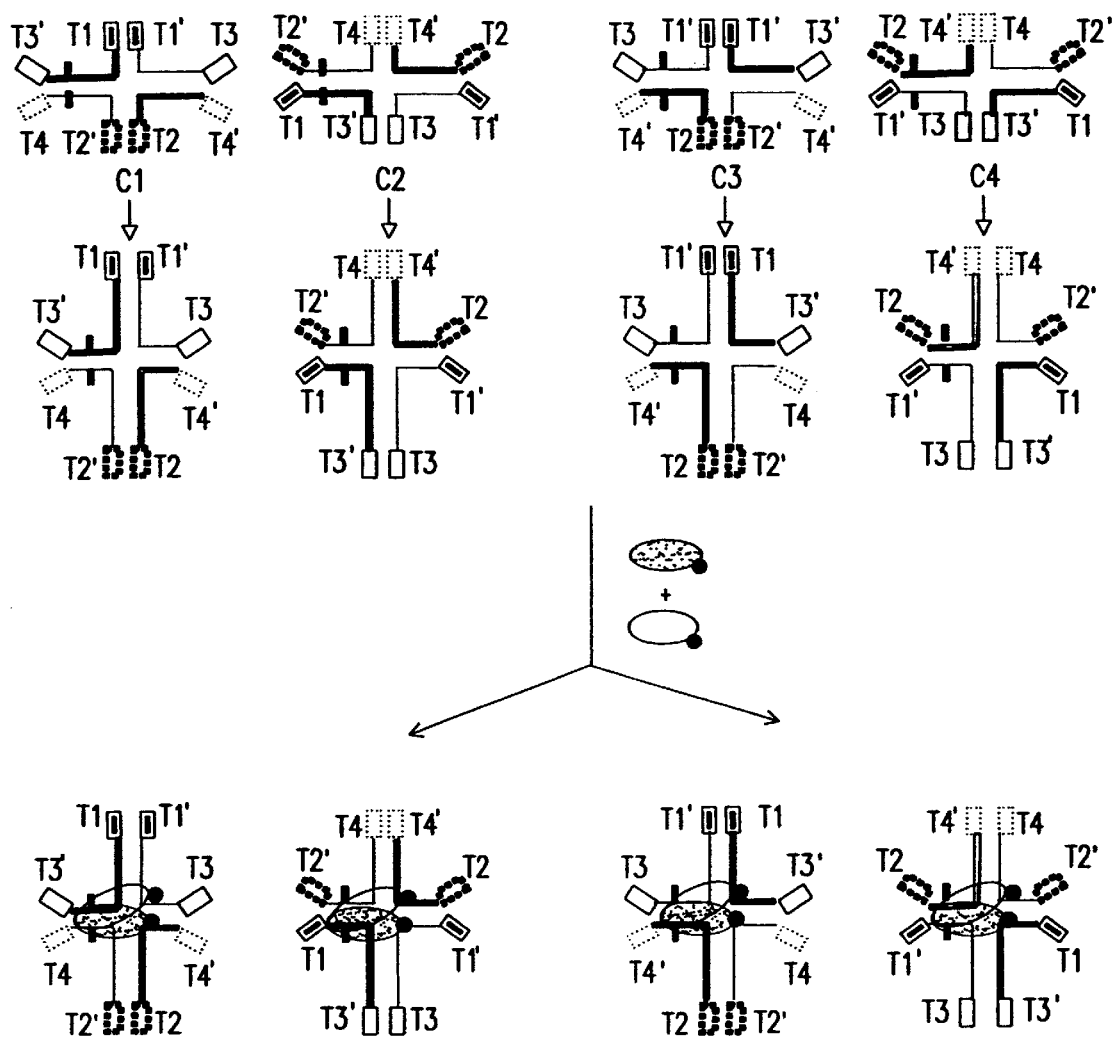

In a preferred embodiment of the invention, two or more proteins can be used to detect a stabilized Holliday junction. The two proteins can be the same protein or two different proteins, or domains or subunits of a single protein. In some embodiments the two or more proteins can associate to form a dimer or higher order oligomer, and in some embodiments oligomerization is dependent upon binding to a Holliday junction. In a preferred embodiment, the two proteins are labeled with different labels and Holliday-junction-dependent complex formation between these two proteins causes the association of the two labels. The association of the two labels can be used as an indicator for the presence of stable Holliday junctions (FIG. 3).

For example, RuvA and RuvC cannot form a RuvC-RuvA complex by themselves in the absence of Holliday junction. However, both RuvA and RuvC can bind to a Holliday junction simultaneously and form a RuvA-RuvC-Holliday junction complex. Both RuvA and RuvC, as well as many RuvC mutants, have been cloned, over-expressed and purified. In a preferred embodiment of the invention, RuvA and RuvC are each fused with a different fluorophores capable of serving as a donor/acceptor pair for intermolecular fluorescence resonance energy transfer (FRET). Intermolecular FRET can be used to detect the association of a donor/acceptor pair and to characterize the relationship between the molecules. The principles involved in the application of FRET for such purposes are well known in the field of molecular biology. References describing the use of FRET to detect the association of two molecules include, for example, Heim R. 1999. Green Fluorescent Protein Forms for Energy Transfer. Methods in Enzymology 302:408–23; Foerster T. 1948. Ann Phys 2:55; Mitra R D, et al. 1996. Fluorescence resonance energy transfer between blue-emitting and red-shifted excitation derivatives of green fluorescente protein. Gene 173:13–7; and Furey W S, et al. 1998. Use of fluorescence energy transfer to investigate the conformation of DNA substrates to the Klenow fragment. Biochemistry 37(9): 2979–90, all of which are incorporated herein by reference. Only in the presence of Holliday junctions will the RuvA and RuvC fusion proteins associate with one another and produce a specific FRET signal. Detection and/or quantification of the FRET signal is used to detect and/or quantify the presence and amount of stable Holliday junctions. Typically, the binding of the two proteins to a stabilized Holliday junction brings the donor and acceptor pair into close proximity, and the resulting change in emission ratio (ratio of the emission at the maximum emission wavelength of the donor vs. the acceptor) or the resulting change in intensity of the emission at the maximum emission wavelength of the acceptor can be used to measure/quantitate the presence of Holliday junctions.

The invention preferably employs a RuvC mutant that lacks the wild-type form of the enzyme's Holliday junction-specific endonuclease activity but retains the ability to specifically bind Holliday junctions. Such mutants include D7N, E66Q, D138N, D141N, D7N, E66D, D138E, and ruvC51, and are described, for example, in Saito A, et al. 1995. Identification of four acidic amino acids that constitute the catalytic center of the RuvC Holliday junction resolvase. Proc Natl Acad Sci USA 92:7470–4; and Sharples G J, et al. 1993. An *E. coli* RuvC mutant defective in cleavage of synthetic Holliday junctions. Nucleic Acid Research, 21(15): 3359–64.

In a preferred embodiment of the invention the FRET donor and acceptor pair comprise proteins. Particularly suitable proteins include Green Fluorescent Proteins (GFPs) and GFP mutants possessing the appropriate excitation and emission frequencies, some of which are described in the preceding references, e.g., Heim R., supra; Foerster T., supra; Mitra R D, et al., supra; and Furey W S, et al., supra.

Figure 4:
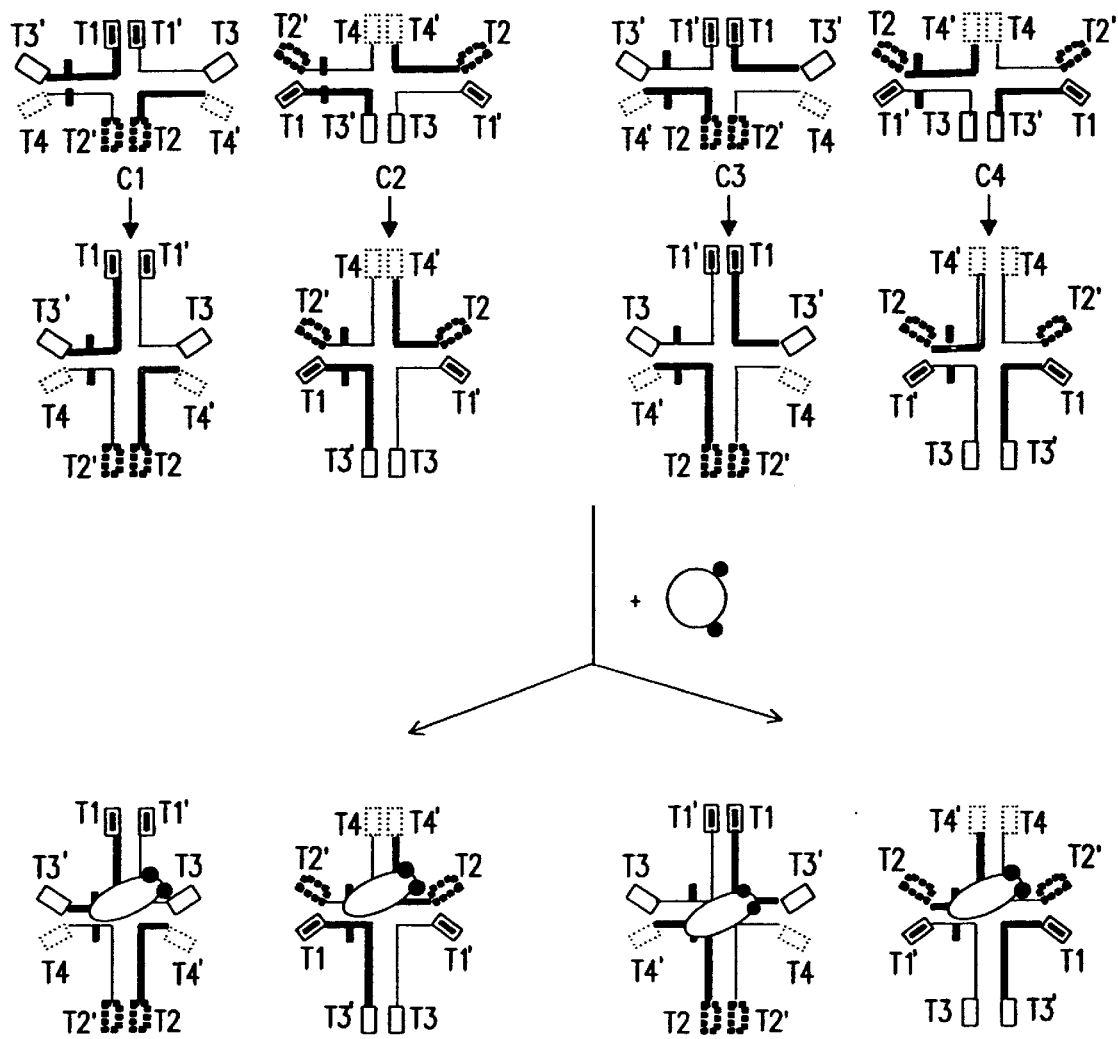

In an embodiment of the invention where detection is achieved by a single Holliday junction-binding protein, intra-molecular FRET can be exploited to detect the presence/quantity of Holliday junctions (FIG. 4). The single Holliday junction-binding protein can be double-labeled with two fluorophores, e.g., two GFP mutants that serve as an intra-molecular donor/acceptor FRET pair. In a preferred embodiment, the single protein used is RuvC, more preferably one of the aforementioned RuvC mutants. The double-labeled protein undergoes a conformational change upon binding to a Holliday junction, which results in a change in the physical relationship between the two fluorophores and hence a change in FRET signal. The change in FRET can be detected and used as an indicator for the presence and the amount of stable Holliday junctions, as described above for the embodiment that employs two Holliday junction binding proteins.

When a single binding protein is used, intermolecular FRET can also be exploited to detect the presence/quantity of Holliday junctions if the protein used can form either homo- or hetero-oligomers (FIG. 3). For example, *E. coli* RuvA exists as a tetramer in solution but can form an octamer upon binding a Holliday junction. Formation of octameric RuvA is dependent on binding a Holliday junction. Therefore, RuvA alone can be used to detect Holliday junctions via inter-molecular FRET. For example, one RuvA tetramer can be labeled with one fluorophore, e.g., a GFPs or a GFP variants, and a second RuvA tetramer can be labeled with a second fluorophore such that the two fluorophores are capable of functioning as an intermolecular donor/acceptor FRET pair. In one such embodiment of the invention, two differentially labeled RuvA tetramers form an octamer in the presence of a Holliday structure.

In an embodiment of the invention a solid surface can act as the label, such as the surface of an optical biosensors, e.g., Biacore or Iasys. Optical biosensors are described, for example, in Canziani G, et al. 1999. Exploring biomolecular recognition using optical biosensors. Methods 19(2): 253–69. Typically, a molecule capable of binding a Holliday junction, preferably including a protein as discussed above, is immobilized on the surface of the biosensor. In this embodiment, the binding of a Holliday junction to the immobilized protein is able to produce a detectable optical signal. The signal can be recorded by the biosensors as an indication of the presence and quantity of stable Holliday junctions. In this embodiment, a single label, i.e., the biosensor surface, is sufficient for the detection of Holliday junctions. One advantage of this embodiment of the invention is that neither the polynucleotides forming the Holliday junction nor the Holliday junction binding molecules need to be labeled.

In another embodiment of the invention, LOCI (Luminescent oxygen channeling immunoassay) can be used to detect the binding of a Holliday-junction binding protein to a Holliday junction. LOCI has been described, for example, in Ulhman E F, et al. 1994. Luminescent oxygen channeling immunoassay: Measurement of particle binding kinetics by chemiluminescence. Proc Natl Acad Sci USA 91:5426–30.

In still another embodiment, detection of the binding of a Holliday-junction binding protein to a Holliday junction can be accomplished by means of an ELISA assay. ELISA assays are well known in the art, and are described, for example, in U.S. Pat. No. 6,013,439 and Sambrook et al., supra.

In yet another embodiment of the invention, mass spectrometry is employed to detect a stabilized Holliday junction. One advantage of this embodiment of the invention is that neither the polynucleotides forming the Holliday junction nor the Holliday junction binding molecules need to be labeled. Molecules with higher mass can be generated by either the formation of a four-way Holliday junction from two duplex DNA or the formation of Holliday junction/protein complex(es) upon binding of Holliday junction specifically binding protein(s) to the Holliday junction. Detection of the existence/ratio of molecules with different masses by mass spectrometry can be used to detect/quantitate Holliday junctions and, in turn, to indicate the presence or absence of differences between two DNA fragments. The use of mass spectrometry to characterize macromolecular complexes is described, for example, in Kelleher N L. 2000. From primary structure to function: biological insights from large-molecule mass spectra. Chem Biol. 7(2): R37–45.

In yet another embodiment of the invention, phenodynamic profiling system from SIGNATUREBIO INC. can be employed to detect Holliday junction induced protein-protein interactions. One advantage of this embodiment of the invention is that neither the polynucleotides forming the Holliday junction nor the Holliday junction binding molecules need to be labeled.

7.3.4.2 Detection of Stabilized Holliday Strucutres By Gel Electrophoresis

In one aspect of the invention, the mixture that results from subjecting the four-way complexes to branch migration conditions is separated by gel electrophoresis. Surprisingly, stabilized Holliday structures can be detected by gel electrophoresis under the appropriate conditions. The presence of a stabilized Holliday structure identified by gel electrophoresis indicates the presence of a difference between the target and reference sequences.

The gel electrophoresis conditions should be chosen so that a stabilized Holliday structure can be resolved from other complexes in the mixture such as duplexes, partial duplexes and single stranded polynucleotides. The actual conditions for gel electrophoresis depend on the size and identity of polynucleotide sequences and the partial duplexes. Such conditions will be apparent to those of skill in the art. For instance, when the target and reference sequence are about 35–300 bp in length and corresponding partial duplexes are about 50–300 bp in length, a stabilized Holliday structure can be resolved in a 4%–6% TBE-PAGE gel at 160V for 30'.

7.3.4.3 Detection By Isolation of Stabilized Holliday Structures

In another aspect of the invention, the stabilized Holliday junction is detected by separating the stabilized Holliday junction from other molecules in the mixture such as duplexes and single stranded polynucleotides. The stabilized Holliday junction may be separated from duplex DNA and isolated by means of gel electrophoresis, capillary electrophoresis, chromatography (including affinity chromatography using columns coated with Holliday-Structure-specifically binding proteins such as those described in detail above).

There are many ways to separate the four-way Holliday structure from duplex DNA. To determine an individual's genotype at multiple SNP positions, a set of PCR primers (F1, F2, R1, and R2) can be designed for each SNP position. DNA fragments (partial duplexes) obtained by PCR using the individual's genomic DNA can be regarded as the target DNA. DNA fragments (partial duplexes) of known genotype obtained by using the same set of primers are regarded as the reference DNA. Therefore, there will be two reference DNA (partial duplexes) for each SNP. The target DNA (partial duplex) at each SNP position is mixed and compared with corresponding two versions of reference DNA (partial duplex), one at a time, by undergoing Holliday junction formation/ branch-migration. After PCR/Branch Migration, the resulting mixtures at multiple (1- millions) SNP positions are pooled together. The pooled DNA is then subjected to conditions (e.g.: gel/capillary electrophoresis, chromatography) that will allow the separation/isolation of Holliday structures. A pool of Holliday structures formed between target DNA and corresponding reference DNA of multiple SNPs is isolated/purified by various means.

Holliday junctions can be separated from duplex DNA by gel electrophoresis or capillary electrophoresis. The band containing Holliday junction DNA can then be identified and isolated. DNA from the band containing Holliday junctions can then be eluted/purified from the gel band.

Alternatively, as another illustration rather than limitation, the pool comprised of Holliday junctions can be isolated by chromatography. In a preferred embodiment, solid surface (e.g.: columns, filters, plastics . . . ) coated/conjugated with a Holliday structure specifically binding protein(s) can be used to isolate/purify Holliday junctions. The existence of DNA fragments of a specific SNP in the purified pool comprised of Holliday junction indicates that the target DNA of that SNP is different from the reference DNA it has been compared with. Or, in other words, the diploid genomic DNA used for generating the target DNA at that specific SNP position has at least one copy of the SNP version that is different from the version of the reference DNA used. Therefore, any method that allows the resolution of the identity of the DNA fragments comprising the isolated/purified pool of Holliday junctions can be used for SNP scoring. Many proteins from various organisms have been shown specifically bind a Holliday junction, and are described in detail above.

As an illustration rather than limitation, DNA hybridization can be used for the resolution of the identity of the DNA fragments comprising the isolated/purified pool of Holliday junctions. In a preferred embodiment, the DNA comprising the isolated Holliday structures can be labeled and used as probes to hybridize with DNA fragments/oligos immobilized on SNP-chips/Micro-arrays for SNP scoring. A positive hybridization signal for a specific SNP on the chip/microarray means that the diploid genomic DNA used for generating the target DNA at that specific SNP position has at least one copy of the SNP version that is different from the version of the reference DNA used. By using all possible versions at each SNP position as reference DNA—one version at a time—to compare with (forming Holliday structure/undergoing branch migration) corresponding target DNA, followed by Holliday structure isolation/purification and identification by hybridization using chip/micro-array, one can determine the genotype of a diploid genomic DNA sample at multiple (1- millions) SNP positions simultaneously with high specificity/accuracy.

Figure 5:
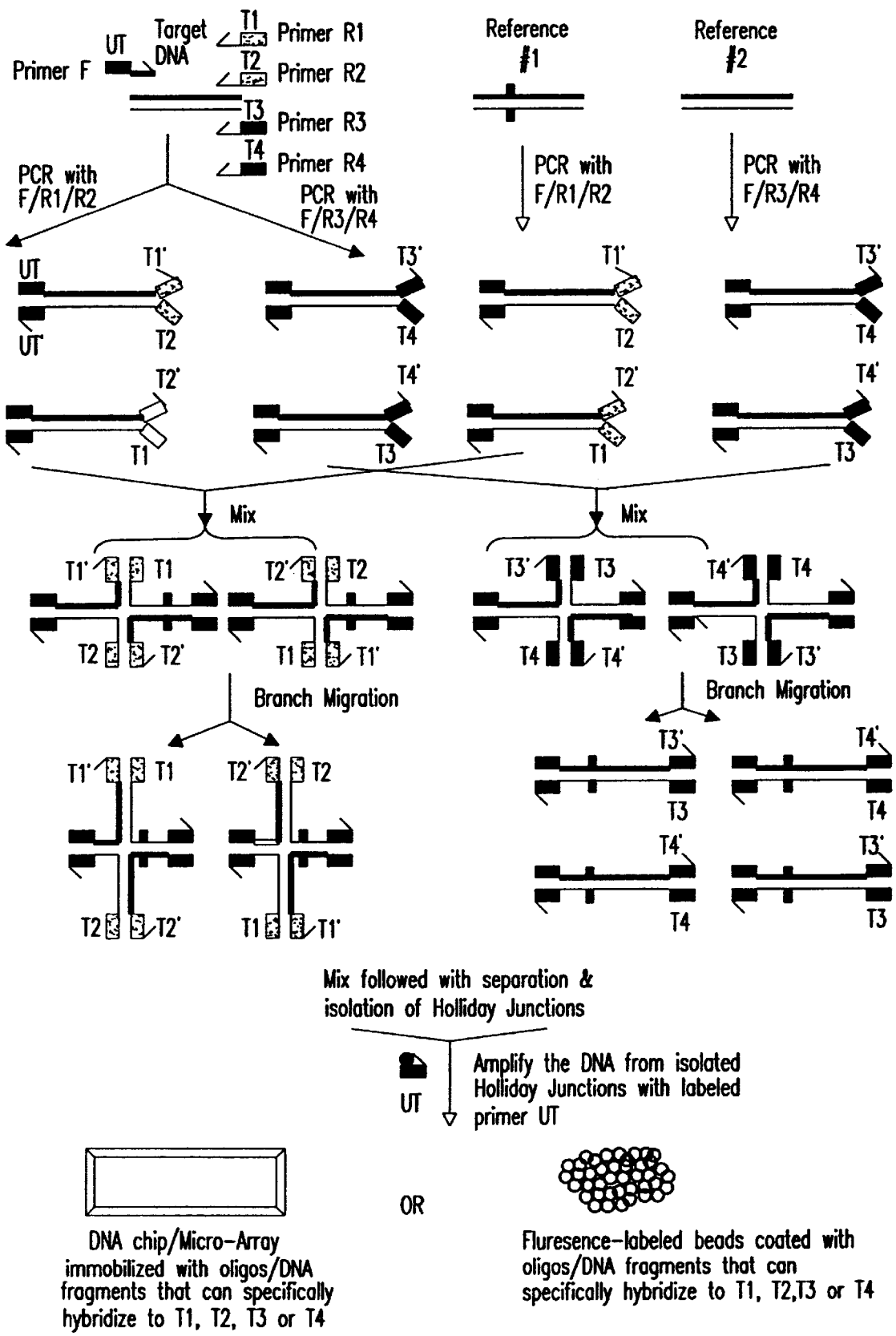

For instance, a method for genotyping multiple polymorphic positions is illustrated in FIG. 5. In FIG. 5, a target DNA is amplified with four forward primers (F/R1, F/R2, F/R3 and F/R4) and one reverse primer. The four forward primers F/R1, F/R2, F/R3 and F/R4 comprise a polynucleotide sequence F that complements the target DNA and one of four tail sequences T1, T2, T3 and T4. The reverse primer comprises a polynucleotide sequence that complements the target DNA and an optional universal tail UT. PCR is carried out as described above to yield target partial duplexes. The forward and reverse primer are chosen so that the resulting partial duplexes include a polymorphism of interest in the target DNA. A reference DNA corresponding to the target DNA and comprising a known sequence at the polymorphism is amplified with the same primers to yield reference partial duplexes. The target duplexes and reference duplexes are mixed under conditions in which four-way structures are capable of forming and in which branch migration can occur. Stabilized Holliday structures can be isolated according to any of the methods described above. Isolation of a Holliday structure indicates a difference between the target sequence and the reference sequence.

Significantly, multiple target DNAs can be assayed simultaneously. Partial duplexes from each unique target DNA are prepared with a unique set of PCR primers. For instance, with two target DNAs, partial duplexes corresponding to a first target DNA can be prepared with primers that correspond to tails T1, T2, T3 and T4. Partial duplexes corresponding to a second target DNA can be prepared with primers that correspond to tails T5, T6, T7 and T8. Tails T1, T2, T3 and T4 should not correspond to tails T5, T6, T7 T8. Reference partial duplexes for each reference DNA are prepared with primers that correspond to the primers used for the corresponding target DNA. All target partial duplexes can be contacted with corresponding reference partial duplexes in the same mixture, and stabilized Holliday structures can be recovered in one step. The recovered polynucleotides can optionally be amplified by PCR using, for instance, the optional universal tail UT. The recovered polynucleotides can then be identified by techniques known to those of skill in the art. For instance, the recovered polynucleotides can be identified by hybridization with oligonucleotides specific for tails T1, T2, T3 and T4 or tails T5, T6, T7 and T8. The hybridization can be carried out with, for example, a gene chip, an array of oligonucleotides or labeled beads coated with the oligonucleotides. The presence of a detectable hybridization signal indicates that a particular target DNA differs from its corresponding reference DNA. For instance, hybridization of recovered polynucleotides to oligonucleotides corresponding to tails T5, T6, T7 and T8 indicates that the second target DNA differed from its corresponding reference DNA.

Significantly, the same detection apparatus (e.g., gene chip, an array of oligonucleotides or labeled beads coated with the oligonucleotides) can be used to genotype any polymorphism. The detection apparatus is specific for the tails corresponding to the PCR primers used in the above method, not for the target DNA.

7.4 Methods of Detecting a Difference Between Two Nucleic Acids By Detecting Stabilized Holliday Structures on Solid Substrates In another aspect, the present invention provides methods and reagents for resolving four-way complexes on solid substrates. One polynucleotide of a partial duplex corresponding to a polynucleotide sequence is immobilized on a solid support and contacted with other polynucleotides from under conditions in which a four-way complex can form and in which branch migration can occur. The sequence can be, for example, a target sequence which forms a four-way complex with a nucleic acid that corresponds to a reference sequence, or vice versa. If the target sequence and reference sequence are identical, then branch migration goes to completion and one duplex is released from the solid surface. If there is a difference between the target sequence and the reference sequence, then branch migration is halted and a Holliday junction structure is stabilized on the solid substrate. Detection of the immobilized Holliday junction structure indicates a difference between the target sequence and the reference sequence.

The solid substrate can be any solid substrate known to those of skill in the art. The solid substrate can comprise any material known to those of skill in the art on which a polynucleotide can be immobilized. Suitable materials include, for example, metals, polymers, glasses, polysaccharides, nitrocellulose and the like. The solid substrate may also take on any form including beads, disks, slabs, strips or any other form capable of bearing polynucleotides. The polynucleotides can be bound to the solid substrate by any means known to those of skill in the art for immobilizing molecules. The polynucleotides may be, for example, noncovalently associated with the solid substrate or covalently associated directly or via a linker. In a preferred embodiment, the polynucleotides are immobilized on nitrocellulose via ultraviolet cross-linking.

Figure 6A:
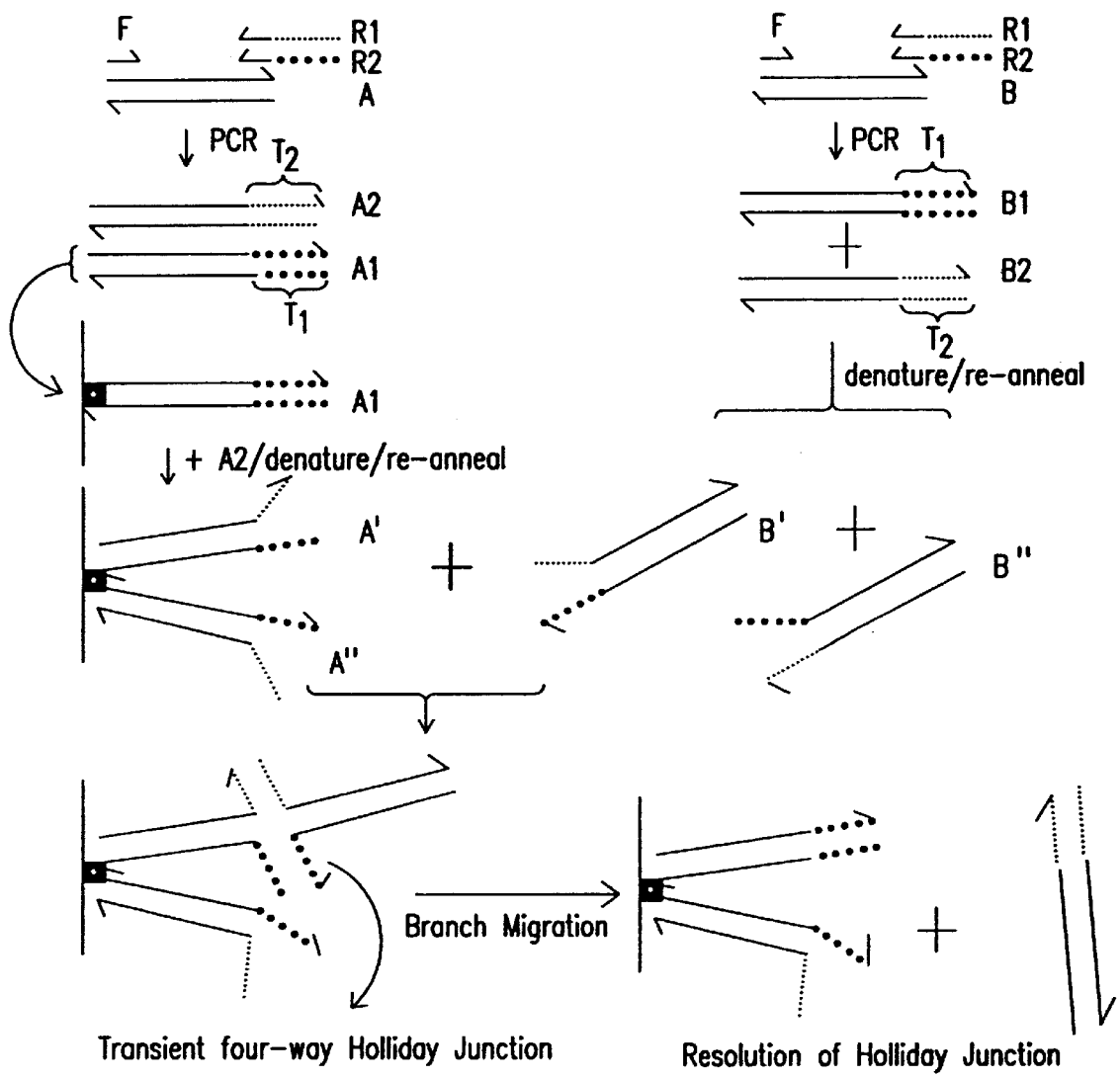
Figure 6B:
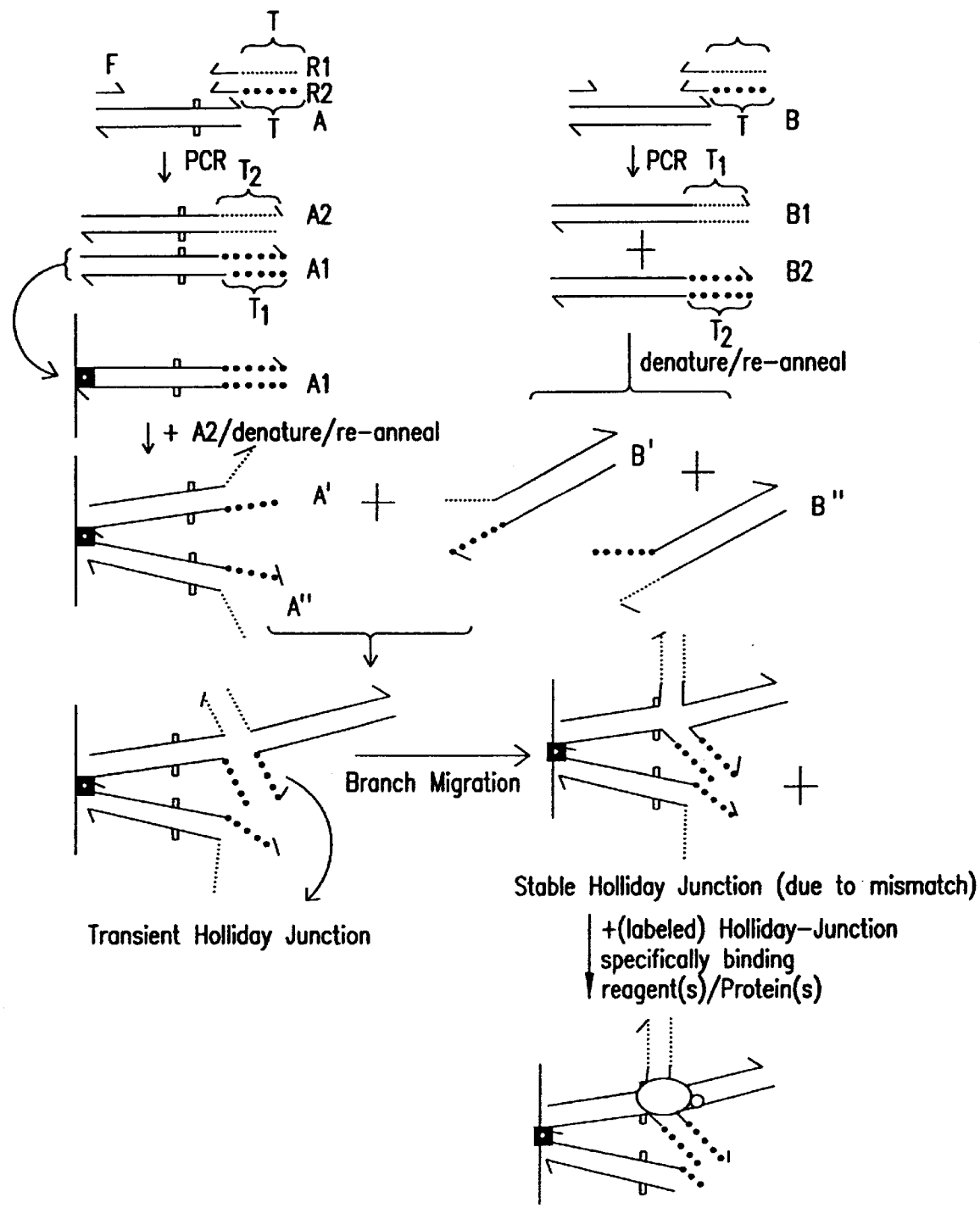

To determine if there is any difference(s)/variation(s) between two DNA fragments A and B, each of the two said DNA fragments (A or B) is first linked with either a tail/tag #1 or a tail/tag #2 through PCR amplification (FIGS. 6A and 6B) using one forward primer (F) and either two of the reverse primers (R1 and R2) (FIGS. 6A and 6B). The resulting 4 DNA duplexes are: A1 (A+tail/tag #1); A2 (A+tail/tag #2); B1 (B+tail/tag #1); and B2 (B+tail/tag #2).

One of the duplexes, for example A1, is immobilized on the solid substrate. The mixture of duplexes A2/B1/B2 is added to immobilized duplex A1 followed by branch migration conditions so that partial duplexes A', A", B', B" can form transient Holliday structures (FIGS. 6A and 6B). If there a mismatch/difference between A and B will the transient Holliday structure become a stabilized Holliday structure/junction (FIG. 6B). When there is no difference between A and B, the transient Holliday structure/junction will resolve into duplexes (FIG. 6A).

Alternatively, one of the duplexes, for example A1, is immobilized on the solid substrate. A1 is then denatured and hybridized with A2 to form partial duplexes A' and A" immobilized on the solid substrate (FIGS. 6A and 6B). A mixture of B1 and B2, preferably at a 1:1 ration, is then subject to boiling/denaturing conditions and then reannealing conditions to form partial duplexes B' and B" form in the mixture (FIGS. 6A and 6B). The B1/B2 mixture that contains B' and B" partial duplexes is then added to the solid substrate with the immobilized A' and A" partial duplexes. The resulting mixture is then subject to branch migration conditions so that partial duplexes A', A", B', B" can form transient Holliday structures (FIGS. 6A and 6B). When there is no difference between A and B, the transient Holliday structure/junction will quickly resolve into duplexes (FIG. 6A).

Any unbound material is then optionally washed from the solid substrate using PCR/Branch migration buffer or any buffer that will not disrupt Holliday structures. Only when there is a mismatch/difference between A and B will stable four-way Holliday structure form on the glass surface that will not be washed away (FIG. 6B).

Reagents are then added to the solid substrate that can not only specifically bind to Holliday structure but can also be detected directly or indirectly. Said reagents include but not limited to GFP (or other fluorescence) labeled Holliday-junction-specifically-binding proteins such as RuvC, RuvA, RusA and their homologues, and other such reagents described in detail above. Any reagents not specifically bound to the surface are then optionally washed. The specifically bound reagent(s) are then detected and/or quantitated by methods appropriate for the reagent. Such methods are described in detail above. Specifically bound reagents indicate the presence of a stabilized Holliday structure on the solid substrate and thereby a difference between A and B.

7.5 Methods of Identifying SNPs

Any genetic variation, including SNPs, involves at least two possible versions for each variable position within a DNA sequence. To determine which versions a target DNA sample (either diploid or haploid) has at a particular variable position, the target DNA sequence(s) are compared with each reference DNA sequences representing all possible versions of variations at that variable position. It is known that DNA variations exist in forms other than SNPs. Not only can this invention detect SNPs, but also, polymorphisms involving multiple bases, multi-base-paired deletions, insertions and mis-sense mutations. However, genotyping by means of SNPs will be used to illustrate, and not limit, an application of this invention to determine the genotypes of various genetic variations of diploid individuals, such as humans.

To determine the genotype of a genomic DNA sample (X/X) at a particular SNP position, the target DNA is amplified from the genomic DNA in question. In addition, two reference DNA (A or B) is amplified from either two reference genomic DNA samples (A/A or B/B) or from cloned DNA fragments containing the two reference DNA sequences (A or B). All three DNA samples are amplified by PCR with two common sets of unlabeled primers under standard PCR conditions. Genomic DNA PCR conditions are similar to PCR conditions for STS (primer concentration for PCR from genomic DNA is ~500 nM–1000 nM for the forward primers and ~250 $\mu$M–500 $\mu$M for each of the two reverse primers), PCR using cloned DNA fragments can tolerate lower primer concentrations (~250 nM.) Each set of primers comprises a total of 3 primers: One forward primer (LF or RF) and two reverse primers (LR1, LR2 or RR1, RR2). LF hybridizes to the target sequence at the left side of the SNP position in question. LF is designed in such a way that it should be at minimum distance from the SNP position in question as far as the feasibility of the PCR amplification is concerned. LF is preferably <10 bp away from the SNP position. LR1 and LR2 share the same 3'-end portion (LR) that hybridizes to the target sequence at the right side of the SNP position in question. LR1/LR2 is designed in such a way that it should be at minimum distance from the SNP position in question as far as the feasibility of the PCR amplification is concerned. The 3' end of LR1/LR2 preferably corresponds to the base pair next to the SNP position in question. RF hybridizes to the target sequence at the left side of the SNP position in question. RF is designed in such a way that it should be at minimum distance from the SNP position in question as far as the feasibility of the PCR amplification is concerned. The 3' end of RF preferably corresponds to the base pair next to the SNP position in question. LR1 and LR2 share the same 3'-end portion (RR) that hybridizes to the target sequence at the right side of the SNP position in question. RR1/RR2 is designed in such a way that it should be at minimum distance from the SNP position in question as far as the feasibility of the PCR amplification is concerned. The 3' end of RR1/RR2 should generally be between 5 and 500 bps, and preferably less than 10 bp.

Figure 7:
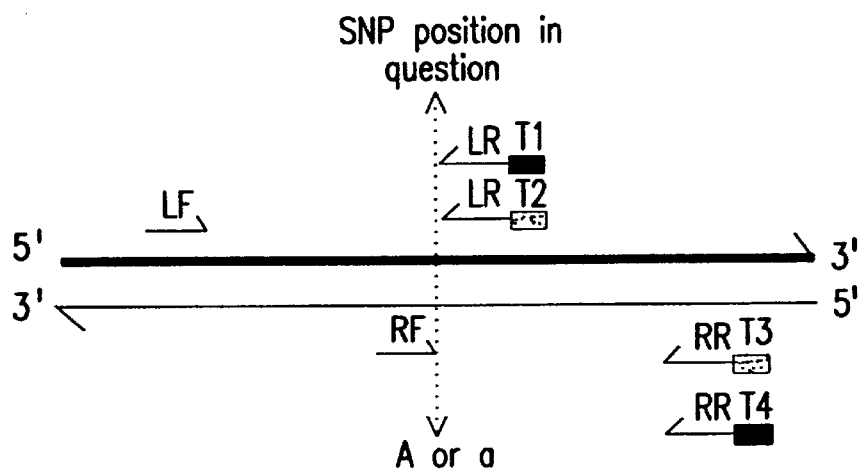

There are two resulting target DNA amplicons—L(X/X) and R(X/X)—amplified from the target genomic DNA sample by using two sets of primers (LF/LR1/LR2 and RF/RR1/RR2). Amplicon L(X/X) is obtained by using primer set LF/LR1/LR2. Amplicon R(X/X) is obtained by using primer set RF/RR1/RR2. There are four reference DNA amplicons—L(A/A), R(A/A), L(B/B), R(B/B)—from two reference DNA samples (A/A and B/B) by using two sets of primers (LF/LR1/LR2 and RF/RR1/RR2). Amplicon L(X/X) is mixed separately at 1:1 ratio with amplicon L(A/A) and amplicon L(B/B) to form mixture L(X/X)/(A/A) and L(X/X)/(B/B). Amplicon R(X/X) is mixed separately at 1:1 ratio with amplicon R(A/A) and amplicon R(B/B) to form mixture R(X/X)/(A/A) and R(X/X)/(B/B). The resulting four mixtures—L(X/X)/(A/A), L(X/X)/(B/B), R(X/X)/(A/A) and R(X/X)/(B/B)—are then denatured/re-annealed and subjected to branch migration conditions (95° C. for 2 min, followed by 65° C. 30' in PCR buffer with Mg++.) The presence and amount of stable Holliday junctions are then detected using Holliday junction specifically binding protein (s) as described earlier. The detected signals of the four mixtures are recorded and compared with the bar codes for all possible genotypes (FIG. 7 and Table 1) to determine the genotype of the target genomic DNA sample at the SNP position in question. This invention will not only allow the determination of the genotype of the target genomic DNA sample at the SNP position in question but will also determine the presence and location of other mutation(s) in the vicinity of the SNP in question.

8. EXAMPLE 1

Detection of A Difference Between Two Sequences By Gel Electrophoresis

This example demonstrates that stabilized Holliday structures can be formed from polynucleotides with differing sequences. The stabilized Holliday structures can be detected by gel electrophoresis according to the methods of the present invention. Five regions of human genomic DNA that contain known single-nucleotide polymorphisms (SNPs) were PCR-amplified using tailed reverse primers to allow the formation of Holliday junctions. The sequence of these regions, the location and identity of the respective SNPs within them and the sequences of the primers can be found in the National Center for Biotechnology Information (NCBI) SNP database. The NCBI assay ID's of the SNPs used were as follows: 4215, 4217, 4213, 4141 and 4212.

Genomic DNA samples from the M08PDR panel (the smallest subset of the Human Polymorphism Discovery Resource panel containing eight individual DNA samples) were purchased from Coriell Cell Repository (Camden, N.J.). Two genomic DNA samples were amplified for each SNP, one homozygote and one heterozygote. The genotypes of these samples are described in Lishanski, 2000, Clinical Chemistry 46 (9), 1464–1470. The primer sequences for amplifying genomic DNA were as follows.

SNP 4215
F: 5'-CTGTGTTATTTGCTGATCCTG-3'(SEQ ID NO: 1)
Rt1: 5'-ACCATGCTCGAGATTACGAGGTAAACTTT CTGAGCCTCTGG-3'(SEQ ID NO: 2)
Rt2: 5'-GATCCTAGGCCTCACGTATTGTAAACTTT CTGAGCCTCTGG-3'(SEQ ID NO: 3)
SNP 4217
F: 5'-CATTAGCTTAAAAGCTGTCTTTTGC-3'(SEQ ID NO: 4)
Rt1: 5'-ACCATGCTCGAGATTACGAGGGTTTGCTG GAAGAAAGCAG-3'(SEQ ID NO: 5)
Rt2: 5'-GATCCTAGGCCTCACGTATTGGTTTGCTGG AAGAAAGCAG-3'(SEQ ID NO: 6)
SNP 4213
F: 5'-AAAACCCTGTTGATATTGGCC-3'(SEQ ID NO: 7)
Rt1: 5'-ACCATGCTCGAGATTACGAGCTGAATACT CTCCATCCTTGCC-3'(SEQ ID NO: 8)
Rt2: 5'-GATCCTAGGCCTCACGTATTCTGAATACTC TCCATCCTTGCC-3'(SEQ ID NO: 9)
SNP 4141
F: 5'-ACCACATCCTCTCATTCGTTG-3'(SEQ ID NO: 10)
Rt1: 5'-ACCATGCTCGAGATTACGAGGGGGTCTCT GCAGTTAACCA-3'(SEQ ID NO: 11)
Rt2: 5'-GATCCTAGGCCTCACGTATTGGGGTCTCT GCAGTTAACCA-3'(SEQ ID NO: 12)
SNP 4212
F: 5'-TGATGTCAAAATAGCTCCATGC-3'(SEQ ID NO: 13)
Rt1: 5'-ACCATGCTCGAGATTACGAGAATATGCAA AGTAATTTTCTGGCC-3'(SEQ ID NO: 14)
Rt2: 5'-GATCCTAGGCCTCACGTATTAATATGCAAA GTAATTTTCTGGCC-3'(SEQ ID NO: 15)

where F is the forward PCR primer, R is the reverse PCR primer, t1 and t2 are the "tail" sequences (underlined) that are common for all 5 amplicons. The forward and reverse primer sequences are published in NCBI SNP database.

PCR amplifications were carried out using a PTC-200 DNA Engine thermocycler (MJ Research Inc., Waltham, Mass.). 35 PCR cycles were performed with 10 s denaturation at 94° C., 15 S reannealing at 62° C. and 45 s extension at 72° C. The cycling was preceded by a 10-min incubation at 95° C. to activate AmpliTaq Gold™ DNA polymerase (Applied Biosystems, Foster City, Calif.) and followed by 2 min of denaturation at 95° C. and 30-min incubation at 65° C. (reannealing and branch migration). The reaction mixtures (100 μl) contained 100 ng genomic DNA, 2.5 U AmpliTaq Gold™ DNA polymerase, 200 μM each dNTP and 250 nM each primer in the commercial AmpliTaq buffer (10 mM Tris-HCl, pH 8.3, 50 mM KCl, 1.5 mM $MgCl_2$, 0.01% gelatin).

5 μl of PCR products subjected to branch migration were mixed with 1 μl of 6×TBE loading buffer (Invitrogen Corp., San Diego, Calif.) and loaded onto a 4–12% gradient TBE pre-cast polyacrylamide gel (Invitrogen Corp., San Diego, Calif.). The gel was run in 1 ×TBE buffer at 165 V for 30 min using an Xcell SureLock™ Mini-Cell electrophoresis apparatus (Invitrogen Corp., San Diego, Calif.). The gel was stained with SYBR Gold fluorescent dye (Molecular Probes, Eugene, Oreg.), and the bands were visualized on the DR-45M Dark Readers transilluminator (Clare Chemical Research, Denver, Colo.).

Figure 8A:
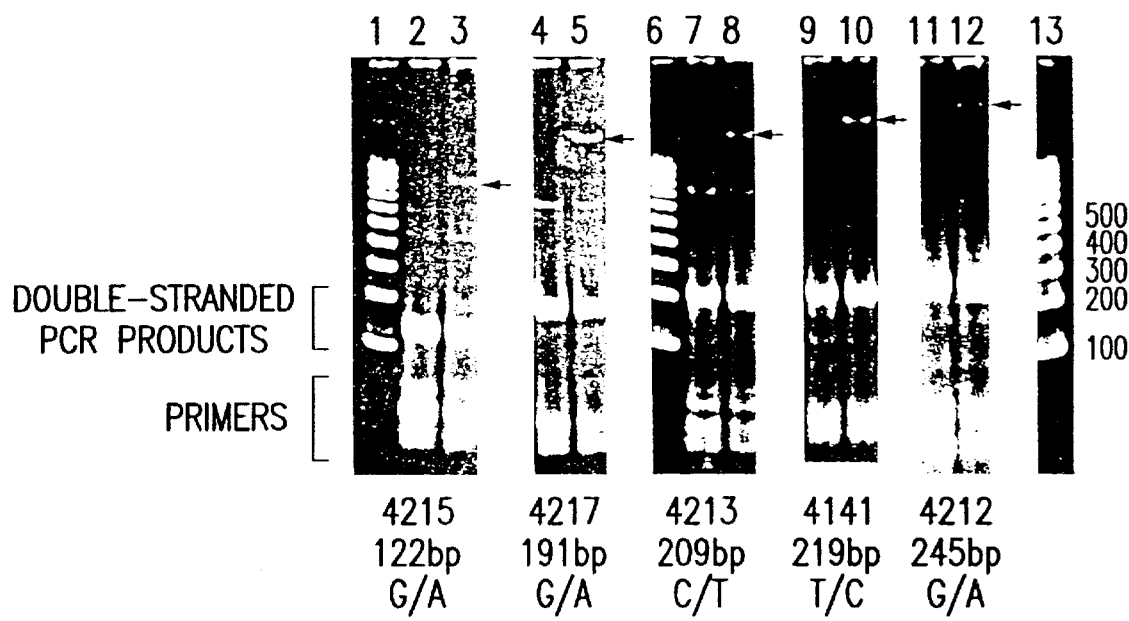

FIG. 8A shows a typical gel picture. A 4–12% gradient pre-cast gel was run in 1×TBE buffer for 30 min at 165 V and stained with SYBR Gold. The NCBI assay ID's, respective polymorphisms and amplicon lengths are shown at the bottom of the gel. Lanes 1, 6 and 13 contain a size marker, the 100 bp DNA ladder (Invitrogen Corp., San Diego, Calif.). Arrows indicate unresolved Holliday junction bands.

For each SNP in FIG. 8A, two lanes are shown: one for a homozygote (left) and another for a heterozygote (right). The amplicon length varies from 122 bp to 245 bp. The relatively faint slowly moving bands (indicated by arrows) are present only in the samples heterozygous for each SNP, when there is a single-base sequence difference between the two alleles. Slower bands correspond to longer amplicons. A serial dilution experiment (not shown) demonstrated that the amount of DNA in these bands is approximately equal to the expected amount of unresolved Holliday junctions (1/16 of the total material). The slowly moving bands disappear upon digestion with the wild type E. coli RuvC protein that is a Holliday junction-specific endonuclease (not shown). Based on this evidence, the slowly moving band clearly represents the unresolved Holliday junctions and is, therefore, indicative of the presence of two alternative alleles in genomic DNA.

Figure 8B:
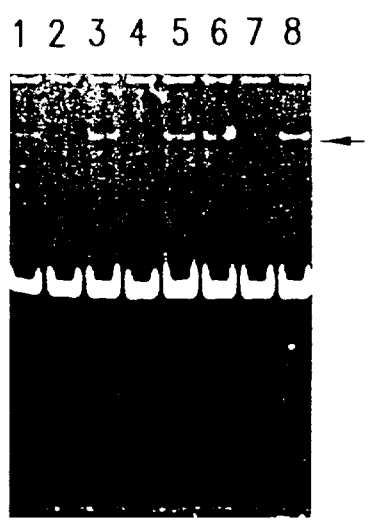

Therefore, a quick electrophoretic run of unlabeled PCR products is sufficient for SNP genotyping as illustrated by the experiment in FIG. 8B. In this experiment all eight genomic DNA samples from M08PDR panel were amplified using the primer set specific for SNP 4215 and subjected to branch migration. A 6% TBE gel was run in 1×TBE buffer for 30 min at 165 V and stained with SYBR Green. After staining of the 6% TBE gel with SYBR Green (Molecular Probes, Eugene, Oreg.) only the five samples (1,3,5,6 and 8) that were previously identified as heterozygous for the A/G SNP (Lishanski, 2000, supra) displayed the unresolved Holliday junction band that is due to inhibition of branch migration (indicated with an arrow).

9. EXAMPLE 2

RuvA and Mutant RuvC Proteins Specifically Bind Stabilized Holliday Junctions

This Example demonstrates that stabilized Holliday junction structures can be specifically bound and detected by proteins according to the methods of the present invention. In particular, stabilized Holliday junction structures were specifically bound and detected with RuvA and with RuvC.

In E. coli, RuvA and RuvC proteins are part of the multi-subunit RuvABC complex that promotes homologous genetic recombination by resolving Holliday junctions. Shinagawa and Iwasaki, 1996 Trends In Biological Sciences 21, 107–111; Eggleston and West, 2000, J. Biol. Chem. 275, 26467–26476. Their binding to synthetic Holliday junctions in vitro is well studied. Davies and West, 1998, Current Biology 8, 725–727; Whitby et al., 1996, J. Mol. Biol. 264, 878–890. The 22 kDa RuvA protein exists in solution as a homotetramer and binds specifically to synthetic Holliday junctions either as a tetramer or an octamer, depending on the protein concentration. The 19 kDa RuvC protein is a Holliday junction-specific endonuclease or a resolvase that binds to Holliday junctions as a dimer, cleaves them and initiates their resolution. Several mutants of RuvC protein have been isolated that retain their specific binding activity but lack the endonuclease activity. Saito et al., 1995, Biochemistry 92, 7470–7474.

Recombinant Ruv A and RuvC (D7N mutant) proteins that were expressed and purified from E. coli were provided by Dr. Hideo Shinagawa (Osaka University, Japan). PCR amplification and branch migration of selected samples from M08PDR panel were conducted as described in Example 1. In addition to the SNPs 4215, 4212, 4213 and 4141 of Example 1, two more SNPs were included in the experiments: SNPs 3989 and 4216. The following sets of primers were used:

SNP 3989
F: 5'-TGAGAGTAGCTTGGCTGGGT-3'(SEQ ID NO: 16)
Rt1: 5'-ACCATGCTCGAGATTACGAGTTTGGCTTTCA TCTTCCCC-3'(SEQ ID NO: 17)
Rt2: 5'-GATCCTAGGCCTCACGTATTTTTGGCTTTCA TCTTCCCC-3'(SEQ ID NO: 18)
SNP 4216
F: 5'-GCCATTGTAAGATCTGAATGAGG-3'(SEQ ID NO: 19)
Rt1: 5'-ACCATGCTCGAGATTACGAGATGTTTTATGT GGAGAGGTATCTGC-3, (SEQ ID NO: 20)
Rt2: 5'-GATCCTAGGCCTCACGTATTATGTTTTATGT GGAGAGGTATCTGC-3'(SEQ ID NO: 21)

Protein binding was detected by band-shift experiments performed as follows. 5 µl of a PCR product subjected to branch migration was mixed at room temperature with 1 µl 0.25 µM RuvA protein or 1 µl 0.5 µM mutant RuvC protein (diluted in 1×AmpliTaq buffer, see Example 1) and allowed to incubate for 5–10 min. 1 µl of 6×sample loading buffer was added, and the samples were loaded onto pre-cast polyacrylamide gels that were run and stained as described in Example 1.

FIG. 9A illustrates the experiment that compares RuvA and RuvC binding to the samples that are homozygous (left) or heterozygous (right) for SNP 4215. The samples (A=RuvA; C=mutant RuvC) were run in a gradient 4–12% polyacrylamide gel in 1×TBE buffer for 30 min at 165 V and the gel was stained with SYBR Green. The positions of rather pale Holliday junction bands are indicated by white dots. No binding (no shifted bands) was observed for the homozygote, whereas the mobility of the Holliday junction band in the heterozygous sample was shifted upon protein binding.

FIG. 9B shows the binding of RuvA under the conditions that ensure its specificity towards Holliday junctions for four PCR products that correspond to four different SNPs. The experimental conditions were identical to those of FIG. 9A, above. Only heterozygous samples were used in this binding experiment. For all the SNPs, the Holliday junction band underwent a change in electrophoretic mobility upon RuvA binding (–indicates no RuvA and+indicates RuvA added).

FIG. 9C provides yet another example of RuvA, mutant RuvC and the mixture of these two proteins binding to Holliday junctions for three PCR products that correspond to three different SNPs in a heterozygous form. The experimental conditions were identical to those of FIG. 9A, above, except that the gel was run for 75 min and stained with SYBR Gold. A=RuvA; C=mutant RuvC; A+C=RuvA+ RuvC (PCR products were added to pre-mixed proteins).

The experiments in this Example show that under certain conditions (relatively low protein concentration) RuvA and mutant RuvC bind specifically to the unresolved Holliday junctions formed by PCR-amplified DNA subjected to branch migration. Therefore, these binding reactions can be used to distinguish the samples that have two alleles of a given polymorphism from those that have one allele or, in other words, for SNP genotyping.

10. EXAMPLE 3

Specific Binding of a Stabilized Holliday Structure by RuvA and RuvC

This example demonstrates that a stabilized Holliday structure can be specifically bound by a complex of two proteins as described in the methods of the present invention. Specific binding of a Holliday structure simultaneously by two proteins, RuvA and mutant RuvC, was demonstrated by probing the Holliday structure with antisera against the two proteins (provided by Dr. Hideo Shinagawa, Osaka University, Japan).

Protein binding was performed as described in Example 2. A sample heterozygous for SNP 4216 was used. When both RuvA and mutant RuvC were included in the binding reaction, they were pre-mixed before the addition of PCR product. Gel electrophoresis conditions were identical to those of FIG. 9C. After staining with SYBR Gold, the gel was incubated briefly in 1×Tris-Glycine running buffer (25 mM Tris base, 192 mM glycine, pH 8.3, Invitrogen Corp., San Diego, Calif.) containing 0. 1% SDS. Electrophoretic transfer of proteins from this gel onto a nitrocellulose membrane (0.2 Jim pore size) was conducted using an Xcell II™ Blot Module (Invitrogen Corp., San Diego, Calif.) at 20 V for 2 hr. The transfer buffer was 12 mM Tris base- 96 mM Glycine (pH 8.3), 20% Methanol. The membrane was briefly rinsed in 1×TBST buffer (Roche Molecular Biochemicals, Mannheim, Germany) that contained 50 mM Tris-HCl, pH 7.5, 150 mM NaCl, 0.05% Tween 20. Then the membrane was incubated in 1% blocking reagent (Roche Molecular Biochemicals, Mannheim, Germany) in 1×TBST for 1 hr. This step and all the incubation and washing steps below were conducted under constant shaking at 4° C. After the blocking step the membrane was incubated for 1 hr in 10 ml of 1:1000 dilution of rabbit anti-RuvC antibody in 1% blocking solution. The membrane was washed in four 20 ml changes of 1×TBST, 5–10 min each wash. Then the membrane was incubated in 10 ml of 1:1000 dilution of ImmunoPure™ goat anti-rabbit IgG (alkaline phosphatase conjugate) in 1% blocking solution for 30 min. The membrane was again washed in four 20 ml changes of 1×TBST, 5–10 min each wash. The substrate solution for alkaline phosphatase was prepared by adding 44 µl of 75 mg/ml Nitroblue Tetrazolium Chloride (NBT) and 33 µl of 5-Bromo-4-chloro-3-indolylphosphate p-Toluidine Salt (BCIP) to 10 ml of 0.1 M Tris-HCl, pH 9.5, 0.1 M NaCl, 50 mM $MgCl_2$. Both NBT and BCIP were from Life Technologies, Rockville, Md. The color development occurred within 5–10 min.

The bands containing RuvC protein, thus revealed (lanes 2 and 3 in FIG. 10, panel II), were marked with a pencil. The membrane was then re-blocked and re-probed with 1:2000 dilution of rabbit anti-RuvA antibody as described above.

Figure 10:
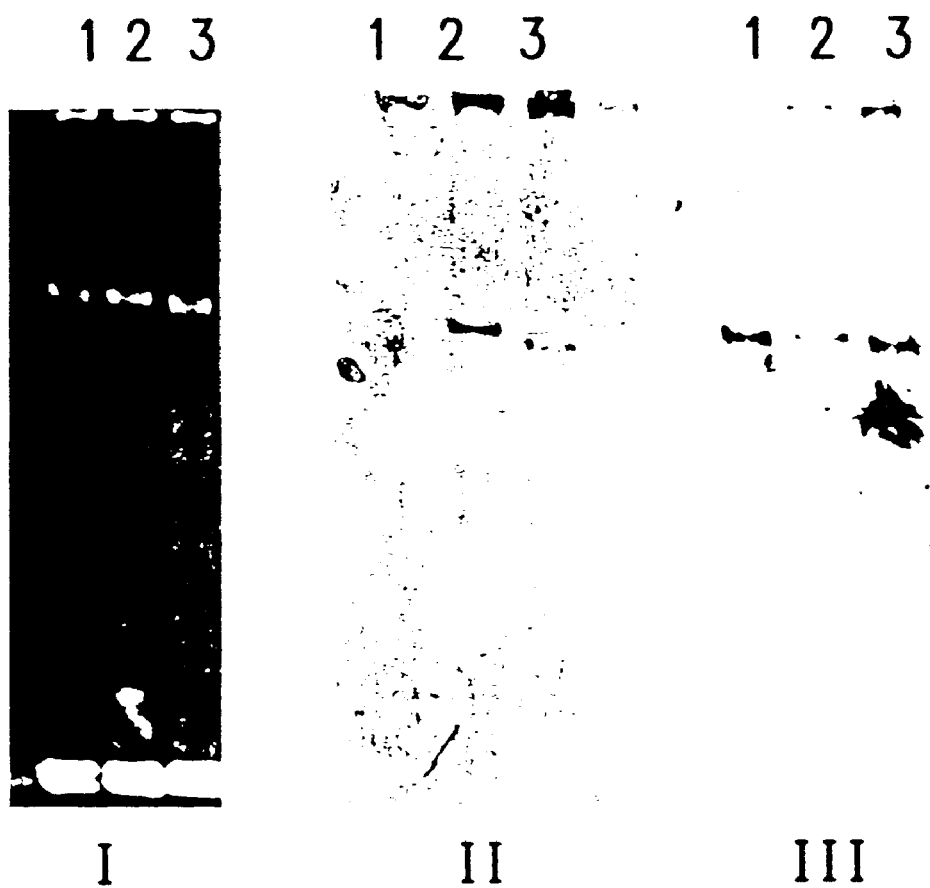
FIG. 10 illustrates the specific interaction of a stable Holliday structure with both RuvA and RuvC.

The bands containing RuvA protein are seen in lanes 1 and 3 (FIG. 10, panel III). The position of the band revealed in lane 3 by the anti-RuvC antibody and then the anti-RuvA antibody, respectively, is exactly the same. Its mobility is just a little higher than the mobilities of the RuvA (lane 1) and RuvC (lane 2) complexes due, probably, to the increased compactness of the RuvAC complex.

In each Panel of FIG. 10, Lane 1 provides heterozygous PCR product+RuvA, Lane 2 provides heterozygous PCR product+RuvC (mutant) and Lane 3 provides heterozygous PCR product+(RuvA+RuvC). Panel I provides the gel stained with SYBR Gold, Panel II mrovides the membrane probed with anti-RuvC antibody and Panel III provides the membrane reprobed with anti-RuvC antibody. Staining with the anti-RuvC antibody is still visible in Lane 2 of Panel III.

11. EXAMPLE 4

Detection of Stabilized Holliday Junctions via LOCI

This Example describes methods of detecting a stabilized Holliday structure by detecting the intermolecular interaction of two molecules with specificity for a Holliday structure.

This Example makes use of the homogeneous chemiluminescent detection method LOCI (Ullman et al., 1994, Proc. Nat. Acad. Sci. USA 91,5426–5430; Packard BioScience, Meriden, Conn.). It makes use of the fact that when two particles, a donor and an acceptor, are in close proximity by virtue of a biological interaction, chemiluminescence is produced. PCR products are prepared from a reference sequence and a target sequence as described in Examples 1–3. The PCR products are contacted under conditions in which four-stranded complexes can form and in which branch migration can occur.

After branch migration, stabilized Holliday junction structures, if any, are contacted with biotinylated RuvA (b-RuvA) and unlabeled mutant RuvC. The complexes are then contacted with antiserum (for instance, mouse or rabbit) specific for RuvC. The resulting complexes are contacted with donor beads coated with streptavidin and acceptor beads coated with anti-mouse or anti-rabbit IgG, as appropriate.

The mixture is then illuminated with laser light at 680 nm, which produces singlet oxygen in a photosensitizer in the donor bead. Singlet oxygen induces chemiluminescence in the compound in the acceptor bead. Signal is observed if stabilized Holliday structures were formed because of a difference between the reference polynucleotide and the target polynucleotide. In the absence of Holliday junctions (no inhibition of branch migration) no signal is observed.

12. EXAMPLE 5

Detection of Stabilized Holliday Structures with RuvA

This example deomonstrates that two molecules of the same protein can be individually labeled with different labels and used for the detection of differences between a target polynucleotide and a reference polynucleotide.

RuvA protein exists as a tetramer in solution and two such tetramers bind Holliday junctions to form an octamer. One RuvA tetramer is labeled in vitro with biotin (b-RuvA) and another tetramer is labeled with fluorescein (f-RuvA). The labeled RuvA molecules can be used to detect stabilized Holliday structures.

PCR products are prepared as described in Examples 1–4 and subject to branch migration conditions. Stabilized Holliday structures, if any, are contacted with b-RuvA and f-RuvA. The resulting mixture is then contacted with donor beads coated with streptavidin and acceptor beads coated with anti-fluorescein antibody. The interaction of the donor beads and acceptor beads is detected as described in Example 4. The presence of a donor-acceptor signal indicates a difference between the target sequence and the reference sequence.

13. EXAMPLE 6

Detection of Stabilized Holliday Structures via FRET

This Example describes an efficient and sensitive method of detecting a difference between two polynucleotides based on Fluorescence Resonance Energy Transfer (FRET).

The published crystal structure of RuvA complex with a synthetic Holliday junction (Rafferty et al., 1996, Science 274, 415–421; Hargreaves et al., 1998, Nature Struct. Biol. 6, 441–446; Ariyoshi et al., 2000, Proc. Nat. Acad. Sci. USA 97, 8257–8262; Roe et al., 1998, Mol. Cell 2, 361–372) indicates that the distance between two RuvA tetramers may be within the FRET range of 10–100 Å.

In order to generate a FRET signal in the presence of a stabilized Holliday structure RuvA in one tetramer is labeled with a donor member of a FRET pair, e.g. fluorescein, and RuvA in the second tetramer is labeled with a corresponding acceptor member, such as tetramethylrhodamine or QSY 7 dye (Molecular Probes, Eugene, Oreg.).

PCR products are prepared as described in Examples 1–4 and subject to branch migration conditions. Stabilized Holliday structures, if any, are contacted with both labeled RuvA tetramers. After binding, the donor fluorophore is excited with an appropriate wavelength using a spectrofluorometer and FRET is detected by the appearance of sensitized fluorescence of the acceptor.

In the absence of Holliday junctions (no branch migration inhibition in PCR products) no FRET is observed. The presence of a FRET signal indicates a stabilized Holliday structure and a difference between the two polynucleotide sequences.

Alternatively, in similar methods, other pairs of molecules that specifically interact with a Holliday are labeled with FRET pairs. For instance, RuvA and mutant RuvC are labeled with two different fluorescent dyes that constitute a FRET pair, and their assembly on Holliday junctions is detected.

In another alternative, the donor and acceptor fluorophores are introduced into RuvA by fusing RuvA molecules with two different mutants of GFP (Heim, 1999, in Methods in Enzymology 302,408–423; Green Fluorescent Protein). Vectors for cloning and expression of such fusions are available from Aurora Bioscience (San Diego, Calif.). This approach eliminates the necessity to chemically modify the protein. Alternatively, RuvA and mutant RuvC are fused to two different GFP mutants and their assembly on Holliday junctions detected.

14. EXAMPLE 7

Detection of Stabilized Holliday Structures via BRET

This example provides another sensitive and efficient method for detecting differenences between polynucleotide sequences. The method in this Example is based on Bioluminescence Resonance Energy Transfer (BRET; Packard BioScience, Meriden Conn.). In the BRET method, energy transfer from a bioluminescent donor luciferase to an acceptor GFP is detected.

PCR products are prepared as described in Examples 1–6 and subject to branch migration conditions. Stabilized Holliday structures, if any, are contacted with both a RuvA fused to luciferase and a RuvA fused to GFP. Fusions of RuvA with luciferase and GFP, respectively, are prepared with commercially available cloning and expression vectors.).

After binding, the donor fluorophore is excited with an appropriate wavelength using a spectrofluorometer and BRET is detected by the appearance of sensitized fluorescence of the acceptor. No excitation light source is required for the detection of the BRET signal. The presence of the BRET signal indicates a difference between the polynucleotide sequences.

Alternatively, RuvA and mutant RuvC can be fused to luciferase and GFP, respectively (or vice versa), and their assembly on Holliday junctions detected by BRET.

The above discussion includes certain theories as to mechanisms involved in the present invention. These theories are not intended and should not be construed to limit the present invention in any way.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are hereby incorporated by reference in their entireties.

What is claimed is:

1. A method for detecting the presence of a difference between two related nucleic acids said method comprising:
   a. forming a four-way complex comprising both of said nucleic acids in duplex form;
   b. subjecting said four-way complex to branch migration conditions wherein, if a difference between said two related nucleic acid is present, branch migration in said four-way complex ceases and said four-way complex is stabilized, and wherein, if no difference between said two related nucleic acid is present, branch migration in said four-way complex continues until complete strand exchange occurs and said four-way complex resolves into two duplex nucleic acids,
   c. subjecting said stabilized complex or its resolved duplex nucleic acids after branch migration to conditions allowing the specific binding of a first reagent that selectively recognizes a four-way complex, wherein the binding of said reagent to said four-way complex produces a detectable signal; and
   d. detecting the signal produced upon the specific binding of said first reagent to said four-way complex as indicative of the presence of said four-way complex, the signal thereof being related to the presence of said difference between said nucleic acid sequences and the failure to detect said signal thereof being related to the lack of difference between said nucleic acid sequences.

2. The method of claim 1 wherein said difference is a mutation.

3. The method of claim 1 wherein said nucleic acids are DNA.

4. The method of claim 1 wherein said four-way complex comprises a Holliday junction.

5. The method of claim 1, wherein said first reagent is a chemical that binds to a Holliday junction and produces a specific, detectable signal upon binding to a Holliday junction.

6. The method of claim 5, wherein said first reagent is a dye.

7. The method of claim 1 wherein said first reagent is a Holliday junction-binding protein.

8. The method of claim 7, wherein said Holliday junction-binding protein is a recombinase or a resolvase.

9. The method of claim 7 wherein said Holliday junction-binding protein is thermostable.

10. The method of claim 7, where said Holliday junction-binding protein is selected from the group consisting of RuvA, RuvC, RuvB, RusA, RuvG, Ccel and spCcel, Hjc.

11. The method of claim 5, wherein said detectable signal involves a conformational change in said Holliday junction-binding protein.

12. The method of claim 1, wherein said detectable signal involves a Holliday junction induced association between said Holliday junction binding protein(s) and said nucleic acids forming said Holliday junction complex.

13. The method of claim 1, wherein said detectable signal involves a specific Holliday-junction-binding-induced fluorescence of said first reagent.

14. The method of claim 1, wherein at least one of the related nucleic acids is not detectably labeled.

15. The method of claim 14, wherein neither of the related nucleic acids is detectably labeled.

16. The method of claim 1, wherein:
   a. said stabilized complex is subjected to conditions allowing the specific binding of a second reagent that selectively recognizes a four-way complex, wherein the concurrent binding of said first and second reagents to said four-way complex produces a detectable signal; and
   b. the signal produced upon the specific binding of said first and second reagents to said four-way complex is detected as indicative of the presence of said four-way complex, the signal thereof being related to the presence of said difference between said nucleic acids and the failure to detect said signal thereof being related to the lack of difference between said nucleic acids.

17. The method of claim 9, wherein said first and second reagents are Holliday-junction binding proteins.

18. The method of claim 9, wherein said signal is produced by Holliday junction-induced close association between said first and second reagents.

* * * * *

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: Artificial sequences: Primers

<400> SEQUENCE: 1
ctgtgttatt tgctgatcct g                                              21

<210> SEQ ID NO 2
<211> LENGTH: 41
<212> TYPE: DNA
<213> ORGANISM: Artificial Sequence
<220> FEATURE:
<223> OTHER INFORMATION: Artificial sequences: Primers

<400> SEQUENCE: 2
```

```
accatgctcg agattacgag gtaaactttc tgagcctctg g                          41

<210> SEQ ID NO 3
<211> LENGTH: 41
<212> TYPE: DNA
<213> ORGANISM: Artificial Sequence
<220> FEATURE:
<223> OTHER INFORMATION: Artificial sequences: Primers

<400> SEQUENCE: 3
gatcctaggc ctcacgtatt gtaaactttc tgagcctctg g                          41

<210> SEQ ID NO 4
<211> LENGTH: 25
<212> TYPE: DNA
<213> ORGANISM: Artificial Sequence
<220> FEATURE:
<223> OTHER INFORMATION: Artificial sequences: Primers

<400> SEQUENCE: 4
cattagctta aaagctgtct tttgc                                            25

<210> SEQ ID NO 5
<211> LENGTH: 40
<212> TYPE: DNA
<213> ORGANISM: Artificial Sequence
<220> FEATURE:
<223> OTHER INFORMATION: Artificial sequences: Primers

<400> SEQUENCE: 5
accatgctcg agattacgag ggtttgctgg aagaaagcag                            40

<210> SEQ ID NO 6
<211> LENGTH: 40
<212> TYPE: DNA
<213> ORGANISM: Artificial Sequence
<220> FEATURE:
<223> OTHER INFORMATION: Artificial sequences: Primers

<400> SEQUENCE: 6
gatcctaggc ctcacgtatt ggtttgctgg aagaaagcag                            40

<210> SEQ ID NO 7
<211> LENGTH: 21
<212> TYPE: DNA
<213> ORGANISM: Artificial Sequence
<220> FEATURE:
<223> OTHER INFORMATION: Artificial sequences: Primers

<400> SEQUENCE: 7
aaaaccctgt tgatattggc c                                                21

<210> SEQ ID NO 8
<211> LENGTH: 42
<212> TYPE: DNA
<213> ORGANISM: Artificial Sequence
<220> FEATURE:
<223> OTHER INFORMATION: Artificial sequences: Primers

<400> SEQUENCE: 8
accatgctcg agattacgag ctgaatactc tccatccttg cc                         42

<210> SEQ ID NO 9
<211> LENGTH: 42
<212> TYPE: DNA
```

```
<213> ORGANISM: Artificial Sequence
<220> FEATURE:
<223> OTHER INFORMATION: Artificial sequences: Primers

<400> SEQUENCE: 9
gatcctaggc ctcacgtatt ctgaatactc tccatccttg cc                      42

<210> SEQ ID NO 10
<211> LENGTH: 21
<212> TYPE: DNA
<213> ORGANISM: Artificial Sequence
<220> FEATURE:
<223> OTHER INFORMATION: Artificial sequences: Primers

<400> SEQUENCE: 10
accacatcct ctcattcgtt g                                             21

<210> SEQ ID NO 11
<211> LENGTH: 40
<212> TYPE: DNA
<213> ORGANISM: Artificial Sequence
<220> FEATURE:
<223> OTHER INFORMATION: Artificial sequences: Primers

<400> SEQUENCE: 11
accatgctcg agattacgag ggggtctctg cagttaacca                         40

<210> SEQ ID NO 12
<211> LENGTH: 40
<212> TYPE: DNA
<213> ORGANISM: Artificial Sequence
<220> FEATURE:
<223> OTHER INFORMATION: Artificial sequences: Primers

<400> SEQUENCE: 12
gatcctaggc ctcacgtatt ggggtctctg cagttaacca                         40

<210> SEQ ID NO 13
<211> LENGTH: 22
<212> TYPE: DNA
<213> ORGANISM: Artificial Sequence
<220> FEATURE:
<223> OTHER INFORMATION: Artificial sequences: Primers

<400> SEQUENCE: 13
tgatgtcaaa atagctccat gc                                            22

<210> SEQ ID NO 14
<211> LENGTH: 44
<212> TYPE: DNA
<213> ORGANISM: Artificial Sequence
<220> FEATURE:
<223> OTHER INFORMATION: Artificial sequences: Primers

<400> SEQUENCE: 14
accatgctcg agattacgag aatatgcaaa gtaattttct ggcc                    44

<210> SEQ ID NO 15
<211> LENGTH: 44
<212> TYPE: DNA
<213> ORGANISM: Artificial Sequence
<220> FEATURE:
<223> OTHER INFORMATION: Artificial sequences: Primers

<400> SEQUENCE: 15
gatcctaggc ctcacgtatt aatatgcaaa gtaattttct ggcc                    44
```

<210> SEQ ID NO 16
<211> LENGTH: 20
<212> TYPE: DNA
<213> ORGANISM: Artificial Sequence
<220> FEATURE:
<223> OTHER INFORMATION: Artificial sequences: Primers

<400> SEQUENCE: 16
tgagagtagc ttggctgggt                                                    20

<210> SEQ ID NO 17
<211> LENGTH: 39
<212> TYPE: DNA
<213> ORGANISM: Artificial Sequence
<220> FEATURE:
<223> OTHER INFORMATION: Artificial sequences: Primers

<400> SEQUENCE: 17
accatgctcg agattacgag tttggctttc atcttcccc                               39

<210> SEQ ID NO 18
<211> LENGTH: 39
<212> TYPE: DNA
<213> ORGANISM: Artificial Sequence
<220> FEATURE:
<223> OTHER INFORMATION: Artificial sequences: Primers

<400> SEQUENCE: 18
gatcctaggc ctcacgtatt tttggctttc atcttcccc                               39

<210> SEQ ID NO 19
<211> LENGTH: 23
<212> TYPE: DNA
<213> ORGANISM: Artificial Sequence
<220> FEATURE:
<223> OTHER INFORMATION: Artificial sequences: Primers

<400> SEQUENCE: 19
gccattgtaa gatctgaatg agg                                                23

<210> SEQ ID NO 20
<211> LENGTH: 45
<212> TYPE: DNA
<213> ORGANISM: Artificial Sequence
<220> FEATURE:
<223> OTHER INFORMATION: Artificial sequences: Primers

<400> SEQUENCE: 20
accatgctcg agattacgag atgttttatg tggagaggta tctgc                        45

<210> SEQ ID NO 21
<211> LENGTH: 45
<212> TYPE: DNA
<213> ORGANISM: Artificial Sequence
<220> FEATURE:
<223> OTHER INFORMATION: Artificial sequences: Primers

<400> SEQUENCE: 21
gatcctaggc ctcacgtatt atgttttatg tggagaggta tctgc                        45